United States Patent
Hall et al.

(10) Patent No.: US 9,284,270 B2
(45) Date of Patent: Mar. 15, 2016

(54) BORONIC ACID CATALYSTS AND METHODS OF USE THEREOF FOR ACTIVATION AND TRANSFORMATION OF CARBOXYLIC ACIDS

(75) Inventors: Dennis Hall, Edmonton (CA); Nicolas Gernigon, La Chapelle-sur-Erdre (FR); Raed M. Al-Zoubi, Irbid (JO); Paul D. Thornton, Kingston (CA)

(73) Assignees: The Governers of the University of Alberta, Edmonton, Alberta (CA); Greencentre Canada, Kingston, Ontario (CA)

(*) Notice: Subject to any disclaimer, the term of this patent is extended or adjusted under 35 U.S.C. 154(b) by 162 days.

(21) Appl. No.: 13/985,236

(22) PCT Filed: Feb. 14, 2012

(86) PCT No.: PCT/CA2012/050083
§ 371 (c)(1),
(2), (4) Date: Jan. 27, 2014

(87) PCT Pub. No.: WO2012/109749
PCT Pub. Date: Aug. 23, 2012

(65) Prior Publication Data
US 2014/0142322 A1    May 22, 2014

Related U.S. Application Data

(60) Provisional application No. 61/442,603, filed on Feb. 14, 2011.

(51) Int. Cl.
*C07F 5/02* (2006.01)
*C07D 207/04* (2006.01)
(Continued)

(52) U.S. Cl.
CPC ............ *C07D 207/04* (2013.01); *B01J 31/146* (2013.01); *C07D 209/48* (2013.01); *C07D 295/185* (2013.01); *C07D 307/56* (2013.01); *C07F 5/025* (2013.01); *C07F 5/05* (2013.01); *B01J 2231/4283* (2013.01)

(58) Field of Classification Search
CPC .......... C07F 5/025; C07F 5/05; B01J 31/146; C07D 207/04; C07D 209/48; C07D 295/185; C07D 307/56
USPC ....... 562/7; 549/213; 548/513, 540; 502/150; 252/183.11, 194
See application file for complete search history.

(56) References Cited

U.S. PATENT DOCUMENTS 8,822,720 B2 *  9/2014  Hall et al. .................... 562/7
2010/0056576 A1  3/2010  Burger et al.
(Continued)

FOREIGN PATENT DOCUMENTS

CA         2694114 A1 *  3/2009
WO    WO 2009/078983     6/2009
WO    WO 2009/138375    11/2009

OTHER PUBLICATIONS

Al-Zoubi et al. (2008), "Direct and Waste-Free Amidations and Cycloadditions by Organocatalytic Activation of Carboxylic Acids at Room Temperature," Issue Angew. Chem. Int. Ed., vol. 47, Issue 15, pp. 2876-2879.
Al-Zoubi et al. (2010), "Mild Silver(I)-Mediated Regioselective Iodination and Bromination of Arylboronic Acids," Organic Letters, vol. 12, No. 11, pp. 2480-2483.
Batey et al. (1999), "Alkenyl and Aryl Boronates Mild Nucleophiles for the Stereoselective Formation of Functionalized N-Heterocycles," J. Am. Chem. Soc., 1999, 121 (21), pp. 5075-5076.
Brown et al. (1980), "Hydroboration. 55. Hydroboration of alkynes with dibromoborane-dimethyl sulfide. Convenient preparation of alkenyldibromoboranes," J. Org. Chem., 45 (3), pp. 389-395.
(Continued)

*Primary Examiner* — Porfirio Nazario Gonzalez
(74) *Attorney, Agent, or Firm* — Lathrop & Gage LLP

(57) ABSTRACT

The present application provides methods and catalysts for activation of carboxylic acids for organic reactions. In particular, methods are disclosed for direct nucleophilic addition reactions, such as, amidation reactions with amines, cycloadditions, and conjugate additions, using boronic acid catalysts of formula I, II or III: Also included are novel boronic acid catalysts of formula IV, V and III:

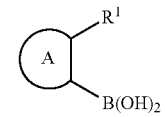

I

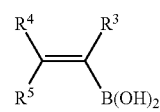

II

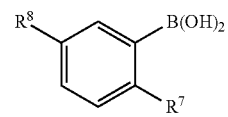

III

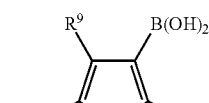

IV

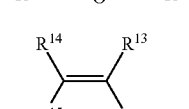

V

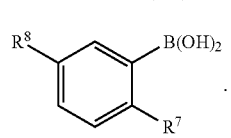

III

21 Claims, 1 Drawing Sheet

(51) Int. Cl.
 C07D 209/48 (2006.01)
 C07F 5/05 (2006.01)
 C07D 295/185 (2006.01)
 C07D 307/56 (2006.01)
 B01J 31/14 (2006.01)

(56) References Cited

U.S. PATENT DOCUMENTS

2010/0197960 A1 8/2010 Hall et al.
2010/0273764 A1 10/2010 Andrews et al.

OTHER PUBLICATIONS

File CAPLUS Document No. (DN) 141:243086 Accession No. (AN) 2004:153807 Entry Date (ED) for STN: Feb. 26, 2004 See Registry No. (RN) 753008-16-1 (Group 2 invention).
File CAPLUS Document No. (DN) 144:350728 Accession No. (AN) 2005:329437 Entry Date (ED) for STN: Apr. 18, 2005 See Registry No. (RN) 216875-62-6 (Group 2 invention).
File CAPLUS Document No. (DN) 149:556434, Accession No. (AN) 2008:1363294 Entry Date (ED) for STN: Nov. 13, 2008 See Registry No. (RN) 1234706-19-4.
File CAPLUS Document No. (DN) 152:525881 Accession No. (AN) 2010:596681 Entry Date (ED) for STN: May 14, 2010 See Registry No. (RN) 406482-19-7 (Group 1 invention).
File CAPLUS Document No. (DN) 153:116308 Accession No. (AN) 2010:188858 Entry Date (ED) for STN: Feb. 12, 2010 See Registry Nos. (RNs) 1233224-65-1 and 1233224-66-2 (Group 2 invention).
File CAPLUS Document No. (DN) 154:10906 Accession No. (AN) 2010:1495326 Entry Date (ED) for STN: Jan. 7, 2011 See Registry No. (RN) 89694-46-2 (Group 1 invention).
File CAPLUS Document No. (DN) 57:16986 Accession No. (AN) 1962:416986 Entry Date (ED) for STN: Apr. 22, 2001 See Registry No. (RN) 89694-44-0 (Group 1 invention).
File Registry Registry No. (RN) 1106677-21-7, Source of Registration (SR): Chemical Library supplied by Aurora Fine Chemicals Entry Date (ED) for STN: Feb. 16, 2009 (Group 1 invention).
File Registry Registry No. (RN) 1217500-68-9, Source of Registration (SR): CAS Client Services Entry Date (ED) for STN: Apr. 8, 2010 (Group 1 invention).
File Registry Registry No. (RN) 1256346-10-7, Source of Registration (SR): CAS Client Services, Entry Date (ED) for STN: Dec. 13, 2010 (Group 1 invention).
File Registry Registry No. (RN) 1256355-01-7 Source of Registration (SR): CAS Client Services Entry Date (ED) for STN: Dec. 13, 2010, (Group 1 invention).
Hara et al. (1990), "$Bf_3$ etherate mediated 1,4-addition of 1-alkenyldialkoxyboranes to $\alpha,\beta$-unsaturated ketones. A stereoselective synthesis of $\gamma, \delta$-Unsaturated ketones," Tetrahedron Letters, vol. 31, Issue 2, 1990, pp. 247-250.
Hara et al. (1998), "The Regioselective 1,4-Addition Reaction of Alkenylboronic Acids to $\alpha,\beta,\alpha',\beta'$-Unsaturated Ketones," Bull. Chem. Soc. Jpn. 1998, 71, 2403-2408.
International Preliminary Report on Patentability issued Aug. 14, 2013 for corresponding International Application No. PCT/CA2012/050083.
International Search Report mailed May 16, 2012 for corresponding International Application No. PCT/CA2012/050083.
Lhermitte et al. (1996), "Radical Reactions in Organoboron Chemistry. III—Addition Reactions to Alkynylboranes as Efficient Routes to New Regio- and Stereodefined Alkenyl Diamino- and Dialkoxyboranes," Synlett, pp. 377-379.
Maki et al. (2005), "N-Alkyl-4-boronopyridinium Halides versus Boric Acid as Catalysts for the Esterification of $\alpha$-Hydroxycarboxylic Acids," Org. Lett., 7 (22), pp. 5047-5050.
Supplementary European Search Report dated Jul. 11, 2014, for corresponding European Patent Application No. 12747236.3.
Szymanska et al. (2009), "3-Substituted phenylalanines as selective AMPA- and kainate receptor ligands" Bioorganic & Medicinal Chemistry 17, pp. 6390-6401.
Thadani et al. (2003), "Diastereoselective allylations and crotylations under phase-transfer conditions using trifluoroborate salts: an application to the total synthesis of (—)-tetrahydrolipstatin," Tetrahedron Letters, vol. 44, Issue 44, pp. 8051-8055.
Trost et al. (1995),"Nickel catalysed coupling of allylamines and boronic acids," J. Chem. Soc., Perkin Trans. 1, 2083-2097.
Waas et al. (1992), "Preparation and Reactions of 1,1-Zinc, Boron and 1,1-Copper, Boron Alkenyl Bimetallics," Tetrahedron Letters, vol. 33, No. 26, pp. 3717-3720.
Written Opinion of the International Searching Authority mailed May 16, 2012, for corresponding International Application No. PCT/CA2012/050083.

* cited by examiner

BORONIC ACID CATALYSTS AND METHODS OF USE THEREOF FOR ACTIVATION AND TRANSFORMATION OF CARBOXYLIC ACIDS

CROSS-REFERENCE TO RELATED APPLICATIONS

This application is a U.S. National Stage application, under 35 U.S.C. 371, of PCT/CA2012/050083, filed in English on Feb. 14, 2012, which claims priority from U.S. provisional application No. 61/442,603, filed on Feb. 14, 2011. Each of these applications is incorporated by reference herein in its entirety.

FIELD OF THE APPLICATION

The present application pertains to the field of boronic acid catalysts and methods for the catalytic activation of carboxylic acids for organic reactions. More particularly, the present application pertains to direct amidation reactions of carboxylic acids with amines.

BACKGROUND

Amide bonds are ubiquitous in nature and represent one of the most important chemical bonds that constitute biomolecules. Amides are present in the backbone of peptides and proteins, and are an important component of polynucleotides. Consequently, the development of synthetic methods for the formation of amide bonds has long preoccupied chemists.

Despite the favorable thermodynamic stability of the resulting amide bond, the dehydrative reaction between a free carboxylic acid and an amine is inhibited by a large activation energy. For instance, the initial formation of a stable ammonium carboxylate salt deters the dehydration step. The salt intermediate collapses to provide the amide product only at very high temperatures (typically over 160° C.) that are incompatible with many functionalized molecules. Consequently, this important reaction continues to challenge chemists. An alternative method for the direct synthesis of an amide bond from a free carboxylic acid and amine in a simple, green and economical fashion would be a very useful tool.

Most current amide bond-forming methods involve the use of large excesses of expensive and toxic reagents such as carbodiimides, carbonyldiimidazole, phosphonium salts, and others, to dehydrate or activate the carboxylic acid. These coupling agents and their associated co-reagents (bases, supernucleophiles, and other additives) generate large amounts of wasteful by-products that tend to complicate the isolation of the desired amide.

The direct formation of amide bonds has been known since 1858 (described in Benz, G. In Comprehensive Organic Synthesis, Vol 6; Trost B. M., Fleming I., Heathcock C. H. Pergamon press: New York, 1991, Chap. 2.3). Catalysts that have been used for amidation reactions between carboxylic acids and amines include: $TiCl_4$ (Carlson et al. Acta Chem. Scand. Ser. B. 1988, 28); $Ti(O-i-Pr)_4$, (Helquist et al. Tetrahedron Lett., 1988, 59, 3049); $Ph_3SbO/P_4S_{10}$ (Matsuda et al. J. Org. Chem. 1991, 56, 4076); $Sb(OEt)_4$ (Yamamoto et al. J. Am. Chem. Soc. 1996, 118, 1569); and $ArB(OH)_2$ (Ishihara et al. J. Org. Chem. 1996, 61, 4196).

The $ArB(OH)_2$ catalysts reported in Ishihara et al. (id) include those where Ar is 3,4,5-trifluorophenyl, 3-nitrophenyl, 3,5-di-(trifluoromethyl)phenyl, 4-trifluoromethylphenyl, phenyl, 2,4,6-tri-(trifluoromethyl)phenyl and 2,3,4,5-tetrafluorophenyl. The reactions were performed at temperatures of about 110° C. (refluxing toluene) with a catalyst loading of 5 mol % and with the removal of water using 4 Å molecular sieves in a Soxhlet thimble. A solid phase version of these catalysts was reported by Latta et al. (Synthesis. 2001, 11, 1611-1613), however the procedure of Latta et al. also requires very high temperatures.

A room temperature catalytic electrophilic activation of carboxylic acids was previously described using ortho-substituted phenyl boronic acids (Hall et al. PCT Patent Application Publication No. WO 2009/030022).

This background information is provided for the purpose of making known information believed by the applicant to be of possible relevance to the present application. No admission is necessarily intended, nor should be construed, that any of the preceding information constitutes prior art against the present application.

SUMMARY OF THE INVENTION

An object of the present invention is to provide boronic acid catalysts capable of activating a carboxylic acid, such that the activated carboxylic acid can be used in a subsequent nucleophilic substitution reaction. The electrophilic activation of carboxylic acids has been achieved using boronic acid catalysts, including 2-halo-5-heteroatom substituent-phenylboronic acids, heteroaryl boronic acids and alkenyl boronic acids.

In accordance with one aspect, there is provided a method for electrophilic activation of a carboxylic acid comprising combining a carboxylic acid-containing compound and a boronic acid compound of formula I, II or III:

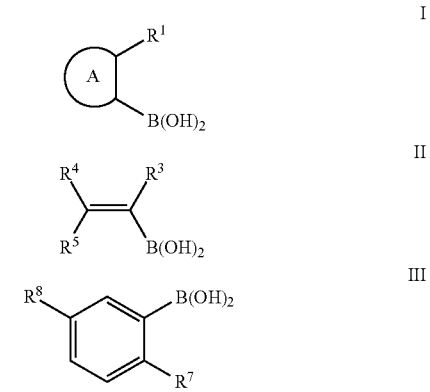

wherein
$R^1$ is a lone pair-containing heteroatom substituent;
A is a 5 or 6-membered heteroaromatic ring comprising at least one heteromoiety selected from O, S, NH or $NC_{1-4}$alkyl in which the $R^1$ and $B(OH)_2$ groups are ortho to each other, and which is optionally substituted with one or more additional substituents independently halo, $R^{2a}$, $C_{1-4}$alkylene$R^{2a}$, $OR^{2a}$, $NR^{2a}R^{2b}$, $SR^{2a}$, $S(O)R^{2a}$, $SO_2R^{2a}$, $SeR^{2a}$ or $PR^{2a}R^{2b}R^{2c}$;
$R^{2a}$, $R^{2b}$ and $R^{2c}$ are independently $C_{1-4}$alkyl or $C_{6-10}$aryl;
at least one of $R^3$ and $R^5$ is a lone pair-containing, heteroatom substituent and the other of $R^3$ and $R^5$ is independently H, halo, $R^{6a}$, $C_{1-4}$alkylene$R^{6a}OR^{6a}$, $NR^{6a}R^{6b}$, $SR^{6a}$, $S(O)R^{6a}$, $SO_2R^{6a}$, $SeR^{6a}$ or $PR^{6a}R^{6b}R^{6c}$;
$R^4$ is H, halo, $R^{6a}$, $C_{1-6}$alkylene$R^{6a}$, $OR^{6a}$, $NR^{6a}R^{6b}$, $SR^{6a}$, $S(O)R^{6a}$, $SO_2R^{6a}$, $SeR^{6a}$ or $PR^{6a}R^{6b}R^{6c}$;

$R^{6a}$, $R^{6b}$ and $R^{6c}$ are independently $C_{1-20}$alkyl or $C_{6-14}$aryl;

$R^7$ is halo;

$R^8$ is $OC_{1-6}$alkyl, $OC_{6-10}$aryl or $OC_{1-4}$alkylene$C_{6-10}$aryl; and each alkyl, aryl and alkylene group is unsubstituted or substituted by one or more halo, $OC_{1-4}$alkyl, $OC_{1-4}$alkylene$C_{6-10}$aryl and/or $OC_{6-10}$aryl, under conditions for the electrophilic activation of the carboxylic acid. In one embodiment, the boronic acid compound is a compound of formula III, wherein $R^8$ is $OC_{5-6}$alkyl or $OC_{1-4}$alkylene$C_{6-10}$aryl.

In accordance with one embodiment, there is provided a method for electrophilic activation of the double or triple bond of α,β-unsaturated carboxylic acids, with applications in 1,4-conjugate additions reactions and other cycloadditions of alkenes and alkynes. The resulting activated carboxylic acids can be used for a variety of subsequent reactions.

In accordance with one embodiment, the activated carboxylic acid can undergo amidation at ambient or near-ambient temperature. The reaction may also occur under mild reaction conditions, and the reactions can be essentially waste free, producing water as the only by-product. In particular room temperature amidation reactions on a variety of carboxylic acids, have been achieved utilizing 2-halo-5-heteroatom substituent-phenylboronic acids, heteroaryl boronic acid and alkenyl boronic acid catalysts.

In accordance with another aspect, there is provided a method for the catalytic electrophilic activation of a carboxylic acid comprising combining the carboxylic acid with a heteroaryl boronic acid of the formula I:

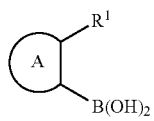

I wherein:

$R^1$ is a lone pair-containing, heteroatom substituent;

A is a 5 or 6-membered heteroaromatic ring comprising at least one heteromoiety selected from O, S, NH and $NC_{1-4}$alkyl in which the $R^1$ and $B(OH)_2$ groups are ortho to each other, and which is optionally substituted with one or more additional substituents independently halo, $R^{2a}$, $C_{1-4}$alkylene$R^{2a}$, $OR^{2a}$, $NR^{2a}R^{2b}$, $SR^{2a}$, $S(O)R^{2a}$, $SO_2R^{2a}$, $SeR^{2a}$ or $PR^{2a}R^{2b}R^{2c}$;

$R^{2a}$, $R^{2b}$ and $R^{2c}$ are independently $C_{1-4}$alkyl or $C_{6-10}$aryl; and each alkyl, aryl and alkylene group is unsubstituted or substituted by one or more halo, $OC_{1-4}$alkyl, $OC_{1-4}$alkylene$C_{6-10}$aryl and/or $OC_{6-10}$aryl, under conditions for the electrophilic activation of the carboxylic acid.

In accordance with another aspect, there is provided a method for the catalytic electrophilic activation of carboxylic acids comprising combining the carboxylic acid and an alkenyl boronic acid of the formula II:

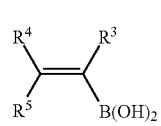

II wherein at least one of $R^3$ and $R^5$ is a lone pair-containing, heteroatom substituent and the other of $R^3$ and $R^5$ is H, halo, $R^{6a}$, $C_{1-4}$alkylene$R^{6a}$, $OR^{6a}$, $NR^{6a}R^{6b}$, $SR^{6a}$, $S(O)R^{6a}$, $SO_2R^{6a}$, $SeR^{6a}$ or $PR^{6a}R^{6b}R^{6c}$;

$R^4$ is H, halo, $R^{6a}$, $C_{1-6}$alkylene$R^{6a}$, $OR^{6a}$, $NR^{6a}R^{6b}$, $SR^{6a}$, $S(O)R^{6a}$, $SO_2R^{6a}$, $SeR^{6a}$ or $PR^{6a}R^{6b}R^{6c}$;

$R^{6a}$, $R^{6b}$ and $R^{6c}$ are independently $C_{1-20}$alkyl or $C_{6-14}$aryl; and each alkyl, aryl and alkylene group is unsubstituted or substituted by one or more halo, $OC_{1-4}$alkyl, $OC_{1-4}$alkylene$C_{6-10}$aryl and/or $OC_{6-10}$aryl, under conditions for the electrophilic activation of the carboxylic acid.

In accordance with one aspect, there is provided a method for the catalytic electrophilic activation of a carboxylic acid comprising combining the carboxylic acid and a phenyl boronic acid of the formula III:

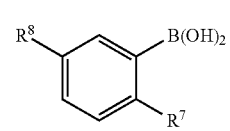

III wherein $R^7$ is halo; and $R^8$ is $OC_{1-6}$alkyl, $OC_{6-10}$aryl or $OC_{1-4}$alkylene$C_{6-10}$aryl, under conditions for the electrophilic activation of the carboxylic acid.

In accordance with one embodiment, the carboxylic acid is activated for reaction with a nucleophile, such as an amine or alcohol. According to this embodiment, the present disclosure, for example, provides a method for the preparation of amides or esters.

In accordance with a further embodiment, the carboxylic acid and amine are both naturally occurring amino acids, or analogs thereof, or protected derivatives thereof. In accordance with a further embodiment, the present methods can be used in the preparation of a dipeptide, polypeptide or protein.

In accordance with one embodiment, the carboxylic acid and boronic acid catalyst of the formula I, II or III may be combined in the presence of a means for removal of water. The means for removal of water may be, for example, the use of molecular sieves, or azeotropic methods such as, for example, a Dean-Stark apparatus.

In accordance with one embodiment, the catalysts of formula I, II or III are attached, for example via a chemical bond, to a solid support.

In accordance with one embodiment, the carboxylic acid is an α,β-unsaturated carboxylic acid that is activated for reaction with a diene in a Diels-Alder reaction or with a nucleophile in a 1,4-conjugate addition reaction.

In accordance with one aspect, there is provided a compound of the formula IV:

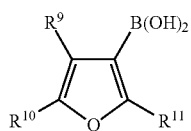

wherein
one of $R^9$ and $R^{11}$ is a lone pair-containing, heteromoiety and the other of $R^9$ and $R^{11}$ is H, halo, $R^{12a}$, $C_{1-4}$alkylene$R^{12a}$, $OR^{12a}$, $NR^{12a}R^{12b}$, $SR^{12a}$, $S(O)R^{12a}$, $SO_2R^{12a}$, $SeR^{12a}$ or $PR^{12a}R^{12b}R^{12c}$;

$R^{10}$ is H, halo, $R^{12a}$, $C_{1-4}$alkylene$R^{12a}$, $OR^{12a}$, $NR^{12a}R^{12b}$, $SR^{12a}$, $S(O)R^{12a}$, $SO_2R^{12a}$, $SeR^{12a}$ or $PR^{2a}R^{2b}R^{2c}$;

$R^{12a}$, $R^{12b}$ and $R^{12c}$ are independently $C_{1-4}$alkyl or $C_{6-10}$aryl; and each alkyl, aryl and alkylene is unsubstituted or substituted by one or more halo, $OC_{1-4}$alkyl, $OC_{1-4}$alkylene$C_{6-10}$aryl and/or $OC_{6-10}$aryl.

In accordance with one aspect, there is provided a compound of the formula V:

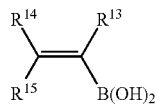

wherein:
$R^{13}$ is a lone pair-containing, heteroatom substituent;

$R^{14}$ and $R^{15}$ are independently H, halo, $R^{16a}$, $C_{1-4}$alkylene$R^{16a}$, $OR^{16a}$, $NR^{16a}R^{16b}$, $SR^{16a}$, $S(O)R^{16a}$, $SO_2R^{16a}$, $SeR^{16a}$ or $SiR^{16a}R^{16b}R^{16c}$;

$R^{16a}$, $R^{16b}$ and $R^{16c}$ are independently $C_{1-20}$alkyl or $C_{6-14}$aryl; and each alkyl, aryl and alkylene group is unsubstituted or substituted by one or more halo, $OC_{1-4}$alkyl, $OC_{1-4}$alkylene$C_{6-10}$aryl and/or $OC_{6-10}$aryl.

In accordance with one aspect, there is provided a compound of the formula III:

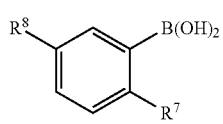

wherein
$R^7$ is halo; and
$R^8$ is $OC_{1-6}$alkyl, $OC_{6-10}$aryl or $OC_{1-4}$alkylene$C_{6-10}$aryl, with the proviso that when $R^7$ is I,
$R^8$ is not OMe.

In accordance with one aspect, there is provided a process for synthesizing a compound of formula IIa

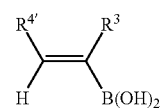

where
$R^3$ is H, halo, $R^{6a}$, $C_{1-4}$alkylene$R^{6a}$, $OR^{6a}$, $NR^{6a}R^{6b}$, $SR^{6a}$, $S(O)R^{6a}$, $SO_2R^{6a}$, $SeR^{6a}$ or $PR^{6a}R^{6b}R^{6c}$;

$R^{6a}$, $R^{6b}$ and $R^{6c}$ are independently $C_{1-20}$alkyl or $C_{6-14}$aryl; and $R^{4'}$ is $C_{1-20}$ alkyl,
comprising reacting a compound of formula X

with $HBBr_2.SMe_2$.

In accordance with one aspect, there is provided a process for synthesizing a compound of formula IIb

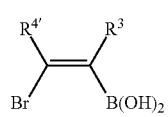

where
$R^3$ is H, halo, $R^{6a}$, $C_{1-4}$alkylene$R^{6a}$, $OR^{6a}$, $NR^{6a}R^{6b}$, $SR^{6a}$, $S(O)R^{6a}$, $SO_2R^{6a}$, $SeR^{6a}$ or $PR^{6a}R^{6b}R^{6c}$;

$R^{6a}$, $R^{6b}$ and $R^{6c}$ are independently $C_{1-20}$alkyl or $C_{6-14}$aryl; and $R^{4'}$ is $C_{1-20}$ alkyl,
comprising reacting a compound of formula X

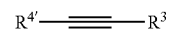

with $BBr_3$ adding a pinacol to the reaction mixture to form a compound of formula XI,

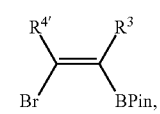

and reacting the compound of formula XI with $NaIO_4$ and HCl.

In accordance with one aspect, there is provided a process for synthesizing a boronic acid of formula Ia

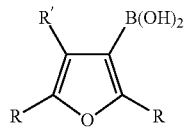

wherein
R' is a lone pair-containing heteromoiety,
each R is independently H, halo, $R^{12a}$, $C_{1-4}$alkylene$R^{12a}$, $OR^{12a}$, $NR^{12a}R^{12b}$, $SR^{12a}$, $S(O)R^{12a}$, $SO_2R^{12a}$, $SeR^{12a}$ or $PR^{12}R^{12b}R^{12c}$; and
$R^{12a}$, $R^{12b}$ and $R^{12c}$ are independently $C_{1-4}$alkyl or $C_{6-10}$aryl;
comprising reacting a compound of formula XII

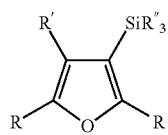

where
R" is $C_{1-4}$ alkyl,
with $BBr_3$ and hydrating the resulting $BBr_2$-substituted furan to give the boronic acid.

In accordance with another aspect, there is provided a catalyst system comprising a boronic acid compound of formula I, II or III, wherein the boronic acid compound is optionally bound or adsorbed to a solid support.

In accordance with another aspect, there is provided a composition comprising a boronic acid compound of formula I, II or III, a carboxylic acid-containing compound and a solvent. The composition can additionally comprise a means for adsorbing water, such as molecular sieves. Optionally, the boronic acid compound of formula I, II or III is bound or adsorbed to a solid support.

Other features and advantages of the present disclosure will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE FIGURES

For a better understanding of the present invention, as well as other aspects and further features thereof, reference is made to the following description which is to be used in conjunction with the accompanying drawings, where.

DETAILED DESCRIPTION

Definitions

Figure 1:
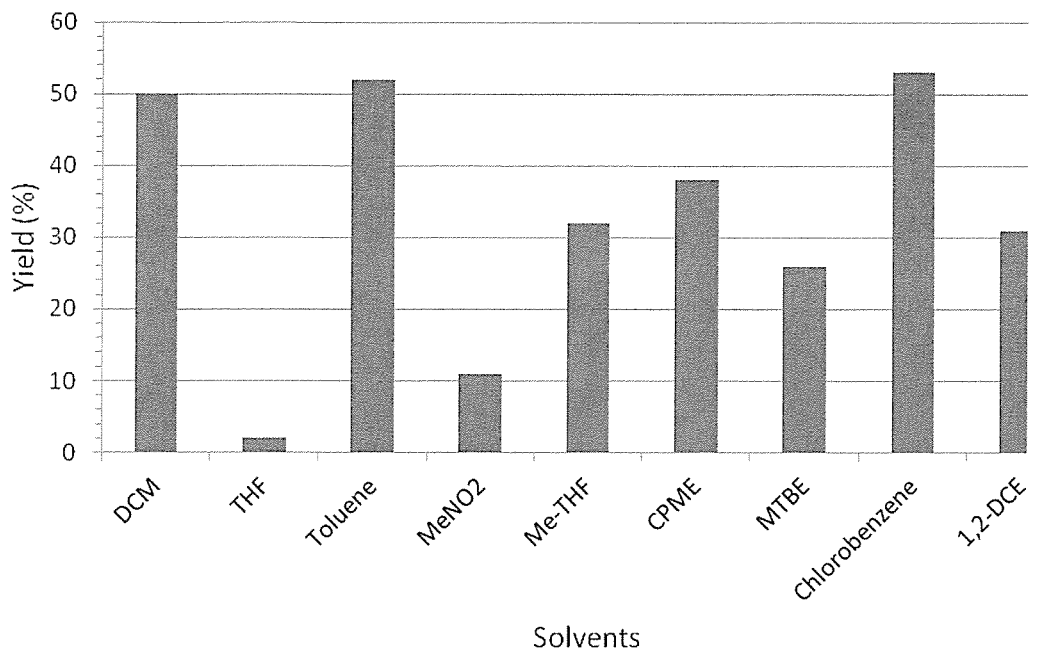
FIG. 1 graphically depicts the results of the solvent screening of Example 18, wherein the percentage yields pertain to the obtained amide for each solvent.

Unless defined otherwise, all technical and scientific terms used herein have the same meaning as commonly understood by one of ordinary skill in the art to which this invention belongs.

As used in the specification and claims, the singular forms "a", "an" and "the" include plural references unless the context clearly dictates otherwise. For example, an embodiment including "a compound" should be understood to present certain aspects with one compound, or two or more additional compounds.

The term "comprising" as used herein will be understood to mean that the list following is non-exhaustive and may or may not include any other additional suitable items, for example one or more further feature(s), component(s) and/or ingredient(s) as appropriate. In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers and/or steps. The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps.

Terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

In embodiments comprising an "additional" or "second" component, such as an additional or second compound, the second component as used herein is chemically different from the other components or first component. A "third" component is different from the other, first, and second components, and further enumerated or "additional" components are similarly different.

The term "suitable" as used herein means that the selection of the particular compound or conditions would depend on the specific synthetic manipulation to be performed, and the identity of the molecule(s) to be transformed, but the selection would be well within the skill of a person trained in the art. All process/method steps described herein are to be conducted under conditions sufficient to provide the product shown or described. A person skilled in the art would understand that all reaction conditions, including, for example, reaction solvent, reaction time, reaction temperature, reaction pressure, reactant ratio and whether or not the reaction should be performed under an anhydrous or inert atmosphere, can be varied to optimize the yield of the desired product and it is within their skill to do so.

As used herein, "alkyl" refers to a linear, branched or cyclic, saturated or unsaturated hydrocarbon group which can be unsubstituted or is optionally substituted with one or more substituent. Examples of saturated straight or branched chain alkyl groups include, but are not limited to, methyl, ethyl, 1-propyl, 2-propyl, 1-butyl, 2-butyl, 2-methyl-1-propyl, 2-methyl-2-propyl, 1-pentyl, 2-pentyl, 3-pentyl, 2-methyl-1-butyl, 3-methyl-1-butyl, 2-methyl-3-butyl, 2,2-dimethyl-1-propyl, 1-hexyl, 2-hexyl, 3-hexyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl and 2-ethyl-1-butyl, 1-heptyl and 1-octyl. As used herein the term "alkyl" encompasses cyclic alkyls, or cycloalkyl groups. The term "cycloalkyl" as used herein refers to a non-aromatic, saturated monocyclic, bicyclic or tricyclic hydrocarbon ring system containing at least 3 carbon atoms. Examples of $C_3$-$C_{12}$ cycloalkyl groups include, but are not limited to, cyclopropyl, cyclobutyl, cyclopentyl, cyclohexyl, cycloheptyl, cyclooctyl, norbornyl, adamantyl, bicyclo[2.2.2]oct-2-enyl, and bicyclo[2.2.2]octyl.

As used herein, the term "alkenyl" refers to a straight, branched or cyclic hydrocarbon group containing at least one double bond which can be unsubstituted or optionally substituted with one or more substituents.

As used herein, the term "alkynyl" refers to an unsaturated, straight or branched chain hydrocarbon group containing at least one triple bond which can be unsubstituted or optionally substituted with one or more substituents.

As used herein, the term "alkenyl" refers to a straight or branched chain hydrocarbon group containing a carbon atom connected by double bonds to two other carbon atoms, which can be unsubstituted or optionally substituted with one or more substituents.

As used herein, the term "aryl" refers to hydrocarbons derived from benzene or a benzene derivative that are unsaturated aromatic carbocyclic groups of from 6 to 100 carbon atoms, or from which may or may not be a fused ring system. In some embodiments the aromatic carbocyclic group comprises 6 to 50 carbon atoms, in other embodiments 6 to 25, and in still other embodiments 6 to 15. The aryls may have a single or multiple rings. The term "aryl" as used herein also includes substituted aryls. Examples include, but are not limited to phenyl, naphthyl, xylene, phenylethane, anthracenyl, 1,2-dihydronaphthyl, 1,2,3,4-tetrahydronaphthyl, fluorenyl, indanyl and indenyl, and the like, all of which can be unsubstituted or substituted.

As used herein, the term "alkylene" refers to a bivalent alkyl group.

As used herein, "heteroaryl" refers to an aryl group that includes from 1 to 10, in other embodiments 1 to 4, heteroatoms selected from, for example, oxygen, nitrogen and sulfur. The heteroaryl group may be substituted or unsubstituted. As used herein, the term "heteroatom" refers to an atom that is not carbon or hydrogen, such as, for example, nitrogen, oxygen, sulfur, phosphorus, chlorine, bromine, and iodine. The term "heteroaromatic ring" as used herein refers to an aromatic ring such as, for example, a five- or six-membered aromatic ring, comprising at least one heteromoiety. The heteroatom moiety may be, for example, O, S, N, NH and $NC_{1-4}$alkyl. A "heteroaromatic group" can include, for example, furanyl, thiophenyl, pyrrolyl, 1,2- or 1,3-oxazolyl, 1,2- or 1,3-diazolyl, 1,2,3- or 1,2,4-triazolyl, and the like. The term "heteromoiety" as used herein means a heteroatom-containing moiety.

As used herein, the term "heterocycle" refers to an aromatic or nonaromatic monocyclic or bicyclic ring of carbon atoms which includes at least one heteroatom, and which can be substituted or unsubstituted. The heterocycle can include, for example, from 1 to 4 heteroatoms or heteromoieties.

Included within the term "heterocycle" are heteroaryls, as defined above. Examples of 3- to 9-membered heterocycles include, but are not limited to, aziridinyl, oxiranyl, thiiranyl, azirinyl, diaziridinyl, diazirinyl, oxaziridinyl, azetidinyl, azetidinonyl, oxetanyl, thietanyl, piperidinyl, piperazinyl, morpholinyl, pyrrolyl, oxazinyl, thiazinyl, diazinyl, triazinyl, tetrazinyl, imidazolyl, benzimidazolyl, tetrazolyl, indolyl, isoquinolinyl, quinolinyl, quinazolinyl, pyrrolidinyl, purinyl, isoxazolyl, benzisoxazolyl, furanyl, furazanyl, pyridinyl, oxazolyl, benzoxazolyl, thiazolyl, benzthiazolyl, thiophenyl, pyrazolyl, triazolyl, benzodiazolyl, benzotriazolyl, pyrimidinyl, isoindolyl and indazolyl.

As used herein, the term "ring system" refers to a carbon-containing ring system containing the specified number of carbon atoms and includes monocyclic and polycyclic rings. Ring systems include saturated, unsaturated or aromatic rings, or mixtures thereof. Where specified the ring system is optionally substituted and/or may optionally contain one or more heteromoieties, such as O, S, N, NH and $NC_{1-4}$alkyl.

The term "polycyclic" as used herein means a group that contains more than one ring linked together and includes, for example, groups that contain two (bicyclic), three (tricyclic) or four (tetracyclic) rings. The rings may be linked through a single bond, a single atom (spirocyclic) or through two atoms (fused and bridged).

As used herein, the term "substituted" refers to the structure having one or more substituents. A substituent is an atom or group of bonded atoms that can be considered to have replaced one or more hydrogen atoms attached to a parent molecular entity. Examples of substituents include aliphatic groups, halogen, arylcarbonyloxy, alkoxycarbonyloxy, aryloxycarbonyloxy, alkoxycarbonyl, aminocarbonyl, alkylthiocarbonyl, alkoxyl, phosphate ester, phosphonato, phosphinato, cyano, tertiary amino, tertiary acylamino, tertiary amide, imino, alkylthio, arylthio, sulfonato, sulfamoyl, tertiary sulfonamido, nitrile, trifluoromethyl, heterocyclyl, aromatic, and heteroaromatic moieties, ether, ester, boron-containing moieties, tertiary phosphines, and silicon-containing moieties. The Willa "optionally substituted" means unsubstituted or substituted.

As used herein, the term "halogen" or "halo" refers to F, Cl, Br or I.

As used herein, the term "fluoro-substituted" refers to a group in which one or more, including all, of the hydrogen atoms have been replaced with a fluorine atom.

As used herein, the term "electrophilic activation" refers to the increased reactivity of a specific atom or functional group (e.g. a carbonyl or carboxyl group) by the removal of electron density from that atom or functional group.

As used herein, the term "lone pair-containing, heteroatom substituent" refers to any chemical group or grouping that comprises at least one heteroatom with one lone pair of electrons and that is capable of donating electron density to neighbouring atoms. Examples of such groups include, but are not limited to, groups comprising, or consisting of, I, Cl, Br, S, O, N, and Se. The heteroatom substituent can further comprise one or more $C_{1-4}$alkyl and/or $C_{6-10}$aryl groups that are optionally further substituted by one or more halo, $C_{1-4}$alkyl and/or $OC_{1-4}$alkyl. In one embodiment, the heteroatom in the lone pair-containing heteroatom substituent is the point of attachment of the substituent to the remainder of the molecule.

As used herein the term "amino acid" refers to any organic compound comprising both a carboxylic acid group and an amine group. This includes compounds wherein there is a single carbon atom between the carboxylic acid group and the amine group, such as α-amino acids, for example many of the naturally occurring amino acids. This term also includes compounds wherein there are two carbon atoms between the carboxylic acid group and the amine group, such as β-amino acids.

As used herein, the term "amino acid analog" refers to any known synthetic or naturally occurring analog of an amino acid as previously defined.

As used herein, the term "protected amino acid" refers to an amino acid or amino acid analog in which the amine and/or the carboxylic acid is protected with a protecting group.

As used herein, the terms "protecting group" or "PG" or the like refer to a chemical moiety that protects or masks a reactive portion of a molecule to prevent side reactions in those reactive portions of the molecule, while manipulating or reacting a different portion of the molecule. After the manipulation or reaction is complete, the protecting group can be removed under conditions that do not degrade or decompose the remaining portions of the molecule. The selection of a suitable protecting group can be made by a person skilled in the art. Many conventional protecting groups are known in the art, for example as described in: "Protective Groups in Organic Chemistry" McOmie, J. F. W. Ed., Plenum Press, 1973; Greene, T. W. and Wuts, P. G. M., "Protective Groups in Organic Synthesis", John Wiley & Sons, 3$^{rd}$ Edition, 1999; and in Kocienski, P. Protecting Groups, 3rd Edition, 2003, Georg Thieme Verlag (The Americas). Examples of suitable protecting groups include but are not limited to t-BOC, Ts, Ms, TBDMS, TBDPS, Tf, Bn, allyl, Fmoc, $C_{1-16}$acyl and the like. t-BOC as used herein refers to the group t-butyloxycarbonyl. Ac as used herein refers to the group acetyl. Ts (tosyl) as used herein refers to the group p-toluenesulfonyl. Ms as used herein refers to the group methanesulfonyl. TBDMS as used herein refers to the group t-butyldimethylsilyl. TBDPS as used herein refers to the group t-butyldiphenylsilyl. Tf as used herein refers to the group trifluoromethanesulfonyl. Ns as used herein refers to the group naphthalene sulphonyl. Bn as used herein refers to the group benzyl. Fmoc as used here refers to the group fluorenylmethoxycarbonyl.

As used herein, the terms "boronic acid compound" or "boronic acid catalyst" are used interchangeably to reference the boronic acid-containing compounds of Formulae I, II and III as defined below. In addition, these terms are used herein to also refer to the boroxine forms and the linear oligomer forms corresponding to the boronic acid-containing compounds of Formula I, II and III. As is well known in the field, boronic acids are usually in equilibrium with their respective boroxines. As a result, the boronic acid compounds described herein can be added to a reaction for electrophilic activation of a carboxylic acid in either their boronic acid form, their boroxine form, or as a mixture of their boronic acid and boroxine forms. By way of example, the following scheme shows a phenyl boronic acid and its corresponding boroxine:

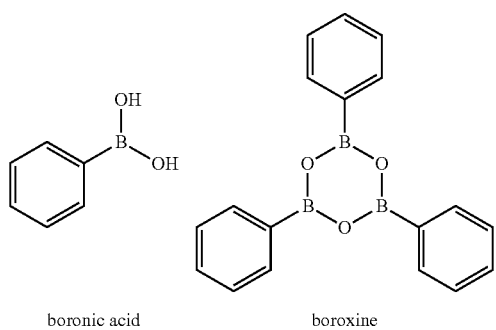 [SMILES: OB(O)c1ccccc1 ; c1ccc(B2OB(c3ccccc3)OB(c3ccccc3)O2)cc1]

boronic acid          boroxine

Described herein are methods for the catalytic activation of carboxylic acids. These activated carboxylic acids can be used for organic reactions, such as nucleophilic substitution or displacement. Also described are methods and catalysts useful in direct amidation reactions of carboxylic acids with amines.

It has been shown that certain boronic acid compounds are capable of catalyzing electrophilic activation of carboxylic acids for organic reactions, including, for example, amidation reactions. In a particular examples, the boronic acid catalysts presently described are capable of catalyzing the reaction of amines (including primary and secondary amines) with carboxylic acids to provide amides. This can further occur in the presence of a means for removal of the water generated in this reaction, for example by the use of molecular sieves or azeotropic methods. Many of these reactions can be performed at room temperature and result in very little waste or by-products.

(a) Heteroaryl Boronic Acid Catalysts

The present application provides a method for catalytic electrophilic activation of a carboxylic acid comprising combining a carboxylic acid-containing compounds and a heteroaryl boronic acid of the formula I:

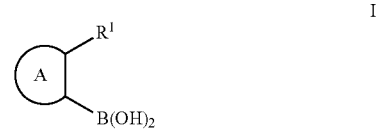

wherein $R^1$ is a lone pair-containing, heteroatom substituent;

A is a 5 or 6-membered heteroaromatic ring comprising at least one heteromoiety selected from O, S, NH and $NC_{1-4}$ alkyl, in which the $R^1$ and $B(OH)_2$ groups are ortho to each other and which is optionally substituted with one or more additional substituents independently selected from halo, $R^{2a}$, $C_{1-4}$alkylene$R^{2a}$, $OR^{2a}$, $NR^{2a}R^{2b}$, $SR^{2a}$, $S(O)R^{2a}$, $SO_2R^{2a}$, $SeR^{2a}$ and $PR^{2a}R^{2b}R^{2c}$;

$R^{2a}$, $R^{2b}$ and $R^{2c}$ are independently $C_{1-4}$alkyl or $C_{6-10}$aryl; and each alkyl, aryl and alkylene group is unsubstituted or substituted by one or more halo, $OC_{1-4}$alkyl, $OC_{1-4}$alkylene$C_{6-10}$aryl and/or $OC_{6-10}$aryl, under conditions for the electrophilic activation of the carboxylic acid.

The boroxine form of the boronic acid of formula I has the following structure:

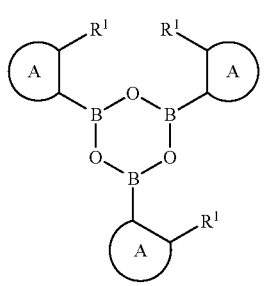

Heteroaryl boronic acids of formula I include those in which A is a 5-membered heteroaromatic ring comprising at least one heteromoiety selected from O, S, NH and $NC_{1-4}$ alkyl. In one embodiment, A is a furan or a thiophene ring. In another embodiment, A is a furan ring.

Heteroaryl boronic acids of formula I can also include those in which $R^1$ is selected from I, Br, Cl and F. In one embodiment, $R^1$ is I or Br. In another embodiment, $R^1$ is I.

Heteroaryl boronic acids of formula I can also include those in which A is substituted with one or two additional substituents independently halo, $R^{2a}$, $C_{1-4}$alkylene$R^{2a}$, $OR^{2a}$, $SR^{2a}$, $S(O)R^{2a}$ or $SO_2R^{2a}$, wherein $R^{2a}$ is methyl, ethyl or phenyl and each methyl, ethyl or phenyl is unsubstituted or substituted by one or more $OC_{1-4}$alkyl, $OC_{1-4}$alkylenePh and/or OPh. A can be substituted with one or two additional substituents such as I, Cl, Me, Et, Ph, $CH_2Ph$, OMe, SMe, S(O)Me and $SO_2Me$, wherein each methyl, ethyl and phenyl group is unsubstituted or substituted by one or more F, Cl, Br, I, OMe, OEt, $OCH_2Ph$ and/or OPh. A can also be unsubstituted.

Some preferred examples of the compound of formula I are:

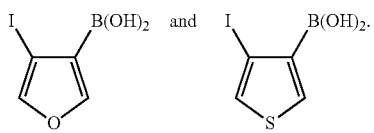 [SMILES: OB(O)c1cocc1I ; OB(O)c1cscc1I]

One preferred example of the compound of formula I is

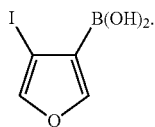

In certain examples, A and/or $R^1$ can also be chiral. In this case, the disclosed methods for carboxylic acid activation can be useful for enantioselective reactions.

Compounds of formula I can be obtained from commercially available sources or they can be prepared, for example, using methods known in the art. For example, furans are available by oxidation of the corresponding 1,4-but-2-endiols (Kraus, G. A. and Wang, X. Synth. Commun. 1998, 28, 1093). Substitution of various functional groups on the furan ring can be accomplished, for example, via transmetalation reactions. Incorporation of the boronic acid group can then be performed, for example, by reacting a corresponding halo (for example iodo) with, for example, an alkyl magnesium chloride followed by trapping with triisopropylborate and acid hydrolysis. Similar boronation reactions can be performed on other 5- and 6-membered heteroaromatic rings, for many of which, the halo precursors are commercially available. Alternatively, halo substitution of 5- and 6-membered heteroaromatic boronic acids may be performed by iodinating an electron-rich heteroaromatic boronic acid, for example using silver (I) mediated regioselective iodination (see Al-Zoubi, R. M. and Hall, D. G. Organic Letters, 2010, 12, 2480-2483).

Also provided herein is a process for synthesizing a compound of formula Ia

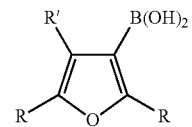

wherein

R' is a lone pair-containing heteromoiety, each R is independently H, halo, $R^{12a}$, $C_{1-4}$alkylene$R^{12a}$, $OR^{12a}$, $NR^{12a}R^{12b}$, $SR^{12a}$, $S(O)R^{12a}$, $SO_2R^{12a}$, $SeR^{12a}$ or $PR^{12a}R^{12b}R^{12c}$; and $R^{12a}$, $R^{12b}$ and $R^{12c}$ are independently $C_{1-4}$alkyl or $C_{6-10}$aryl;

comprising reacting a compound of formula XII

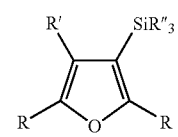

where

R'' is $C_{1-4}$ alkyl, with $BBr_3$ and hydrating the resulting $BBr_2$-substituted furan to give the boronic acid.

(b) Alkenyl Boronic Acid Catalysts

Also described herein are methods for the catalytic electrophilic activation of a carboxylic acid comprising combining the carboxylic acid and an alkenyl boronic acid of the formula II:

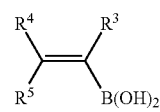

wherein at least one of $R^3$ and $R^5$ is a lone pair-containing, heteroatom substituent and the other of $R^3$ and $R^5$ is H, halo, $R^{6a}$, $C_{1-4}$alkylene$R^{6a}$, $OR^{6a}$, $NR^{6a}R^{6b}$, $SR^{6a}$, $S(O)R^{6a}$, $SO_2R^{6a}$, $SeR^{6a}$ or $PR^{6a}R^{6b}R^{6c}$;

$R^4$ is H, halo, $R^{6a}$, $C_{1-6}$alkylene$R^{6a}$, $OR^{6a}$, $NR^{6a}R^{6b}$, $SR^{6a}$, $S(O)R^{6a}$, $SO_2R^{6a}$, $SeR^{6a}$ or $PR^{6a}R^{6b}R^{6c}$;

$R^{6a}$, $R^{6b}$ and $R^{6c}$ are independently $C_{1-20}$alkyl or $C_{6-14}$aryl; and each alkyl, aryl and alkylene group is unsubstituted or substituted by one or more halo, $OC_{1-4}$alkyl, $OC_{1-4}$alkylene$C_{6-10}$aryl and/or $OC_{6-10}$aryl, under conditions for the electrophilic activation of the carboxylic acid.

The boroxine form of the alkenyl boronic acids of formula II has the following structure:

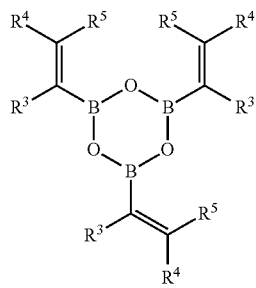

The alkenyl boronic acids of formula II include those in which $R^3$ is a lone pair-containing, electron-rich group selected from I, Br, Cl and F. In one embodiment, $R^3$ is I or Br. In another embodiment, $R^3$ is I.

The alkenyl boronic acids of formula II include those in which $R^5$ is a lone pair-containing, electron-rich group selected from I, Br, Cl and F. In one embodiment, $R^5$ is I or Br.

The alkenyl boronic acids of formula II include those in which $R^4$ and $R^5$ are independently H, halo, $R^{6a}$, $C_{1-6}$alkylene$R^{6a}$, $OR^{6a}$, $SR^{6a}$, $S(O)R^{6a}$ or $SO_2R^{6a}$, and $R^{6a}$, $R^{6b}$ and $R^{6c}$ are independently $C_{1-10}$alkyl or $C_{6-10}$aryl, wherein each alkyl, aryl and alkylene group is unsubstituted or substituted by one or more $OC_{1-4}$alkyl, $OC_{1-4}$alkylenePh and/or OPh. $R^4$ and $R^5$ may also be I, Cl, $C_{1-4}$alkyl, Ph, $CH_2$Ph, OMe, SMe, S(O)Me or $SO_2$Me, wherein each methyl, ethyl or phenyl is unsubstituted or substituted by one or more of F, Br, Cl, I, OMe, OEt, $OCH_2$Ph and/or OPh. In one embodiment, one of $R^4$ and $R^5$ is $C_{1-10}$alkyl and the other is H.

Two preferred examples of compounds of formula II are

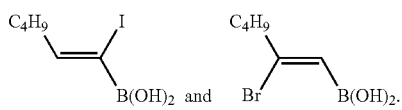

$R^3$, $R^4$ and/or $R^5$ may also be chiral, and the method may therefore useful for the activation of carboxylic acids for enantioselective reactions.

Compounds of formula II are either commercially available or can be prepared using methods known in the art. For example, various substituents may be added to the terminus of an unsubstituted alkyne by reaction with a strong base and a suitable electrophile. The resulting alkyne can be reduced to the alkene using known procedures. Functional groups can be added to the triple bond of an alkyne with reduction to the corresponding alkene. For example, reaction of the alkyne with $HBBr_2.SMe_2$ provides, after suitable workup, the corresponding alkenyl boronic acid. Also, addition of $BBr_3$ to a terminal alkyne results in the cis addition of Br and $BBr_2$ to the triple bond. The resulting $BBr_2$ group may be reacted with a diol, followed by oxidation to provide the desired boronic acid. Various functional groups can be incorporated by transmetalation reactions of with the halogens on either the alkene or alkyne, The boronic acid group may also be incorporated, for example, by reacting a corresponding alkenyl halo (for example iodo) with, for example, an alkyl magnesium chloride followed by trapping with triisopropylborate and acid hydrolysis.

In accordance with one embodiment, there is provided is a process for synthesizing a compound of formula IIa

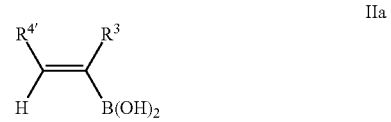

where $R^3$ is H, halo, $R^{6a}$, $C_{1-4}$alkylene$R^{6a}$, $OR^{6a}$, $NR^{6a}R^{6b}$, $SR^{6a}$, $S(O)R^{6a}$, $SO_2R^{6a}$, $SeR^{6a}$ or $PR^{6a}R^{6b}R^{6c}$;

$R^{6a}$, $R^{6b}$ and $R^{6c}$ are independently $C_{1-20}$alkyl or $C_{6-14}$aryl; and $R^{4'}$ is $C_{1-20}$ alkyl, comprising reacting a compound of formula X

with $HBBr_2.SMe_2$.

1. In accordance with another embodiment, there is provided is a process for synthesizing a compound of formula Ib

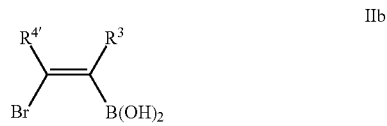

where $R^3$ is H, halo, $R^{6a}$, $C_{1-4}$alkylene$R^{6a}$, $OR^{6a}$, $NR^{6a}R^{6b}$, $SR^{6a}$, $S(O)R^{6a}$, $SO_2R^{6a}$, $SeR^{6a}$ or $PR^{6a}R^{6b}R^{6c}$;

$R^{6a}$, $R^{6b}$ and $R^{6c}$ are independently $C_{1-20}$alkyl or $C_{6-14}$aryl; and $R^{4'}$ is $C_{1-20}$ alkyl, comprising reacting a compound of formula X

with $BBr_3$ adding a pinacol to the reaction mixture to form a compound of formula XI,

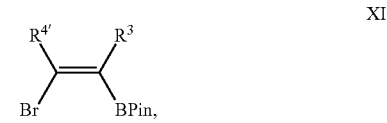

and reacting the compound of formula XI with $NaIO_4$ and HCl.

(c) Phenyl Boronic Acid Catalysts

Also described herein are methods for the catalytic electrophilic activation of a carboxylic acid comprising combining the carboxylic acid and a phenyl boronic acid of the formula III:

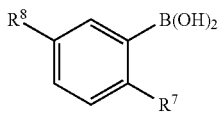

wherein
$R^7$ is halo; and
$R^8$ is $OC_{1-6}$alkyl, $OC_{6-10}$aryl or $OC_{1-4}$alkylene$C_{6-10}$aryl,
under conditions for the electrophilic activation of the carboxylic acid.

The boroxine form of the phenyl boronic acids of formula III has the following structure:

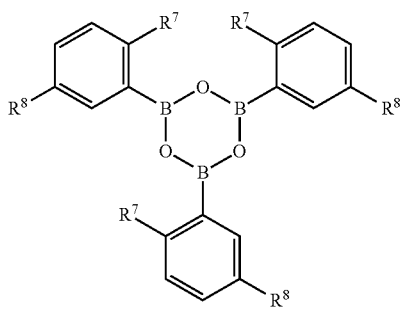

Phenyl boronic acids of formula III include those in which $R^7$ is I. For example, the phenyl boronic acids of formula III include those in which $R^8$ is OMe, OPh or $CH_2Ph$.

Two examples of compounds of formula III are

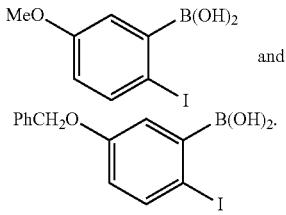

Compounds of formula III are either commercially available or can be prepared using methods known in the art. For example, the boronic acid group may be attached to a suitable substituted phenyl precursor using transmetalation reaction conditions. In one example, a halogen group, such as iodo, may be converted to a Grignard reagent, for example by reaction with phenyl magnesium bromide, and then reacted with a trialkyl borate to produce, under standard reaction conditions, the corresponding the boronic acid. Alternatively, the compounds of formula III can be prepared by iodinating an electron-rich phenyl boronic acid, for example using silver (I) mediated regioselective iodination (see Al-Zoubi, R. M. and Hall, D. G. Organic Letters, 2010, 12, 2480-2483).

(d) Carboxylic Acid Activation and Nucleophilic Addition

As set out above, the boronic acid compounds described herein are useful in catalyzing carboxylic acid activation. The activated carboxylic acid is useful, for example, in nucleophilic addition reactions.

In a preferred embodiment, the carboxylic acid activation and the subsequent nucleophilic addition reaction (e.g., amidation reaction) are performed as a one pot reaction. In this example, selection of the appropriate reaction conditions is made taking into consideration both the nature of the carboxylic acid-containing compound, the nature of the boronic acid catalyst and the nature of the nucleophile, as well as the nature of the product. In this embodiment, the reagents for the activation of the carboxylic acid can be added together with the reagents for the nucleophilic addition, in any order.

In an alternative embodiment, the nucleophilic addition reaction is performed by first premixing the boronic acid catalyst with the carboxylic acid-containing compound and a means for removing water (e.g., molecular sieves) and incubating, or "aging", the resulting mixture for a period of time prior to addition of the nucleophile.

The catalytic activation of a carboxylic acid using the boronic acid catalysts described above, is performed under conditions suitable for carrying out the electrophilic activation of the carboxylic acid. Specifically, selection of the particular reaction conditions, including, for example, solvent(s), reaction temperature, reaction time and reagent ratio and concentration for the electrophilic activation of the carboxylic acid, is within the skill of a worker skilled in the art taking into consideration, for example, the nature of the carboxylic acid-containing compound, the downstream application of the activated carboxylic acid and the catalyst properties. Similarly, the reaction conditions for subsequent reaction of the activated carboxylic acid with a nucleophile, are selected based on, for example, the nature of the nucleophile (e.g., solvent solubility, etc.).

In terms of solvent selection, various organic solvents can be employed. A suitable solvent is any solvent that does not react with the catalyst, or the nucleophile, carboxylic acid or activated carboxylic acid, or any protected derivative thereof. In specific examples, the solvent is not an alcohol.

Examples of suitable solvents include, but are not limited to, methyl t-butyl ether, hexanes, toluene, dichloromethane, tetrahydrofuran, 2-methyl tetrahydrofuran, isopropyl acetate, benzene, dichloroethane, cyclopentyl methyl ether, dimethyl carbonate, diethyl carbonate, methyl isobutyl ketone, methyl ethyl ketone, heptane, xylenes, chloroform, carbon tetrachloride, ethyl acetate, t-butyl acetate, diethyl ether, acetonitrile, propyl acetate, N,N-dimethylformamide, N,N-dimethylacetamide, dimethylsulfoxide, and t-butanol. Ideally, the solvent for the reaction is a "green solvent", wherein a green solvent is generally considered to be a solvent that does not have a negative impact on the environment.

In certain embodiments, the reaction solvent comprises at least one of dichloromethane (DCM or $CH_2Cl_2$), tetrahydrofuran (THF), 2-methyl-THF, fluorobenzene and toluene. Other examples of suitable solvents are toluene, nitromethane, methyl-tetrahydrofuran (Me-THF), cyclopentylmethyl ether (CPME), tert-butylmethyl ether (TBME), chlorobenzene and 1,2-dichloroethane (1,2-DME).

As would also be well understood by a worker skilled in the art, the temperature of the reaction can vary and is selected based on various considerations, such as, for example, ease of reaction, stability of reagents, solubility characteristics, solvent, etc. The temperature used for the reaction is also, at least in part, dependent on the presence and nature of the means for water removal employed during the reaction. In the embodiment in which a means for water removal is employed and that means is azeotropic distillation, the reaction is typically performed at a temperature within the range of about 50° C. to about 140° C. However, it should be understood that this is a non-limiting range since the actual temperature will be dependent on the boiling point of the solvent employed.

In a further embodiment, the reaction includes the use of a adsorbent means for water removal, such as molecular sieves.

In this embodiment, the reaction can be performed at lower temperatures. For example, the reaction temperature can be ambient temperature or room temperature (i.e., about 20° C. to about 27° C.) or slightly above room temperature (i.e., up to about 45° C., or up to about 40° C.).

The length of reaction time will again be dependent on various parameters, including the rate of reaction and the acceptable yield of the reaction. In a specific, non-limiting, embodiment, the reaction time is from about 2 hours to about 50 hours.

In a specific embodiment, the ratio of the nucleophile to carboxylic acid is about 2:1 to about 1:1. In one embodiment, the amount of boronic acid catalyst can be less than about 1 mol %. In alternative embodiments the amount of boronic acid catalyst is from about 1 mol % to about 25 mol %, about 5 mol % to about 25 mol %, or about 10 mol %, relative to the amount of carboxylic acid-containing compound.

The concentration of reagents in the reaction mixture can vary depending on, for example, solubility in solvent and scale of reaction. In embodiments in which the reaction is used in an industrial scale, it is desirable to maximize the concentration of reagents to increase efficiency in teens of cost and/or time and to decrease the amount of solvent employed. The concentration of the reagents can range from about 0.05 M to about 2 M or higher, or from about 0.05 M to about 0.5 M, or about 0.10 M.

A person skilled in the art would appreciate that the conditions for the electrophilic activation of the carboxylic acid can also vary depending on the structure of the carboxylic acid, the reaction to be performed and the specific catalyst selected, and would be able to vary the reaction conditions to obtain an optimum yield of the desired product. Various methods are available for following the course of a reaction and include, for example, chromatographic and spectroscopy techniques.

In certain embodiments, the boronic acid compound of formula I, II or III can be attached to a solid support using known methodologies. Such catalysts are useful, for example, for heterogeneous or homogeneous solid-phase reactions. The solid support may be, for example, but not limited to, silica or a polymeric insoluble matrix such as polystyrene. The boronic acid compound can be attached to the support material at, for example, but not limited to, a functional group that is distal to the boronic acid moiety.

The carboxylic acid used in the presently described methods is electrophilically activated using the compounds of formula I, II or III. The resulting activated carboxylic acid can be used in reactions with a nitrogen nucleophile, such as in an amidation reaction. The nitrogen nucleophile can be, for example, a primary or secondary aliphatic amine or an aromatic amine.

For nucleophilic addition reactions that generate water, for example amidation reactions, the present methods can be performed with a means for removal of the water generated in the reaction. A "means for removal of water" as used herein refers to any method or reagent that does not interfere with the reaction of a nucleophile with the carboxylic acid and which provides an effective removal of the water generated in the present methods. The means for removal of water can be an adsorbent means, such as molecular sieves, for example, 3 Å, 4 Å and/or 5 Å activated molecular sieves (activated by drying in a suitable oven, such as a high temperature oven). Other means for removal of water, can include, for example, drying agents such as activated alumina, benzophenone, bentonite clay, calcium chloride, calcium hydride, calcium sulfate, copper(II) sulfate, lithium chloride, lithium bromide, magnesium, magnesium sulfate, potassium carbonate, silica gel, sodium chlorate and sodium sulfate. Another means for removal of water may be an azeotropic distillation for removal of water during the reaction.

The activated carboxylic acids synthesized with the present methods can be employed in a reaction with a nucleophile. The nucleophile can be any suitable nucleophilic species known to the skilled person. Such a nucleophile can form a covalent linkage to the carbon atom of the activated carboxylic acid group. The nucleophile can be a compound comprising an amine, an alcohol or a thiol. The nucleophile can also be a compound comprising a primary or secondary amine. The nucleophile can also comprise substituted or unsubstituted aryl groups and/or branched and/or unbranched, saturated and/or unsaturated, substituted or unsubstituted, cyclic and/or acyclic alkyl groups.

In the case where the nucleophile is an amine, the amine can be an amino acid such as, for example, one of the naturally occurring amino acids, analogs thereof or protected versions thereof. The methods as presently described can also be used for the preparation of a single amide or peptide bond, or in the synthesis of a dipeptide, polypeptide or protein.

The nucleophile can also be a diol or a diamine and/or the carboxylic acid is a dicarboxylic acid and the presently described methods can result in the formation of polymeric compounds.

The amine can also be attached to a solid support.

The carboxylic acids activated by the present methods can be any suitable carboxylic acid-containing compound known to the skilled person which are capable of forming covalent linkages to, for example, a nucleophile. The carboxylic acid can comprise substituted or unsubstituted aryl groups and/or branched and/or unbranched, saturated and/or unsaturated, substituted or unsubstituted, cyclic and/or acyclic alkyl groups. The carboxylic acid can also be, for example, a naturally occurring amino acid or analog thereof or protected version thereof, and the present methods may be used in the preparation of a single amide or peptide bond, or in the synthesis of a dipeptide, polypeptide or protein. The carboxylic acid can also be attached to a solid support.

A combination of different boronic acid catalysts can also be used in the presently described methods, including combinations of two or more of the compounds of formulae I, II and III.

The boronic acids can be used in their boronic acid form or, as described above, can be added to the activation reaction in their boroxine form or as a mixture of their boronic acid and boroxine forms.

Catalyst Compounds (a) Furanyl Boronic Acids

The present application further provides the boronic acid compound of formula IV:

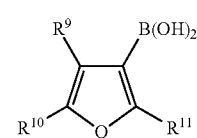

IV wherein
one of $R^9$ and $R^{11}$ is a lone pair-containing, heteroatom substituent and the other of $R^9$ and $R^{11}$ is H, halo, $R^{12a}$, $C_{1-4}$alkyleneR$^{12}$, $SR^{12a}$, $S(O)R^{12a}$, $SO_2R^{12a}$, $SeR^{2a}$ or $PR^{12a}R^{12b}R^{12c}$;
$R^{10}$ is H, halo, $R^{12a}$, $C_{1-4}$alkyleneR$^{12a}$, $OR^{12a}$, $NR^{12a}R^{12b}$, $SR^{12a}$, $S(O)R^{12a}$, $SO_2R^{12a}$, $SeR^{12a}$ or $PR^{12a}R^{12b}R^{12c}$;

$R^{12a}$, $R^{12b}$ and $R^{12c}$ are independently $C_{1-4}$alkyl or $C_{6-10}$aryl; and each alkyl, aryl and alkylene group is unsubstituted or substituted by one or more halo, $OC_{1-4}$alkyl, $OC_{1-4}$alkylene$C_{6-10}$aryl and/or $OC_{6-10}$aryl.

$R^9$ is preferably I, Br, Cl or F. In one preferred embodiment, $R^9$ is I or Br. In another preferred embodiment, $R^9$ is I.

In another embodiment, $R^{10}$ and $R^{11}$ are independently H, halo, $R^{12a}$, $C_{1-4}$alkylene$R^{12a}$, $OR^{12a}$, $SR^{12a}$, $S(O)R^{12a}$, or $SO_2R^{12a}$, wherein $R^{12a}$ is methyl, ethyl or phenyl, wherein each methyl, ethyl or phenyl is unsubstituted or substituted by one or more $OC_{1-4}$alkyl, $OC_{1-4}$alkylenePh and/or OPh. In a further embodiment, $R^{10}$ and $R^{11}$ are independently H, I, Me, Et, Ph, $CH_2Ph$, $C(O)Me$, $CO_2Me$, OMe, SMe, $S(O)Me$ or $SO_2Me$, wherein each methyl, ethyl or phenyl is unsubstituted or substituted by one or more F, Cl, I, Br, OMe, OEt, $OCH_2Ph$ and/or OPh. In a further embodiment only one of $R^{10}$ and $R^{11}$ is I, Cl, Me, Et, Ph, $CH_2Ph$, $C(O)Me$, $CO_2Me$, OMe, SMe, $S(O)Me$ or $SO_2Me$, wherein each methyl, ethyl or phenyl is unsubstituted or substituted by one or more fluoro and the other of $R^{10}$ and $R^{11}$ is H. In a further embodiment $R^{10}$ and $R^{11}$ are both H.

One preferred compound of formula I is:

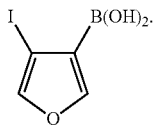

The compounds of formula IV are either commercially available or are prepared using methods known in the art as described above for the compounds of formula I.

(b) Alkenyl Boronic Acids

The present disclosure includes compounds of the formula V:

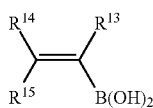

$R^{13}$ is a lone pair-containing, heteroatom substituent;
$R^{14}$ and $R^{15}$ are independently H, halo, $R^{16a}$, $C_{1-6}$alkylene$R^{16a}$, $OR^{16a}$, $NR^{16a}R^{16b}$, $SR^{16a}$, $S(O)R^{16a}$, $SO_2R^{16a}$, $SeR^{16a}$ or $PR^{16a}R^{16b}R^{16c}$;
$R^{16a}$, $R^{16b}$ and $R^{16c}$ are independently $C_{1-20}$alkyl or $C_{6-14}$aryl; and
each alkyl, aryl and alkylene group is unsubstituted or substituted by one or more halo, $OC_{1-4}$alkyl, $OC_{1-4}$alkylene$C_{6-10}$aryl and/or $OC_{6-10}$aryl.

$R^{13}$ can be a lone pair-containing heteroatom, for example an electron-rich group such as, for example, I, Br, Cl or F. In one preferred embodiment, $R^{13}$ is I or Br. In another embodiment, $R^{13}$ is I.

$R^{14}$ and $R^{15}$ are independently H, halo, $R^{16a}$, $C_{1-6}$alkylene$R^{16a}$, $OR^{16a}$, $SR^{16a}$, $S(O)R^{16a}$ or $SO_2R^{16a}$, and $R^{16a}$, wherein $R^{16b}$ and $R^{16c}$ are independently $C_{1-10}$alkyl and $C_{6-10}$aryl; and each alkyl, aryl and alkylene group is unsubstituted or substituted by one or more $OC_{1-4}$alkyl, $OC_{1-4}$alkylenePh and/or OPh. In a further embodiment, $R^{14}$ and $R^{15}$ are independently I, Cl, $C_{1-10}$alkyl, Ph, $CH_2Ph$, $C(O)Me$, $CO_2Me$, OMe, SMe, $S(O)Me$ or $SO_2Me$, wherein each methyl, ethyl or phenyl is unsubstituted or substituted by one or more F, Cl, I, Br, OMe, OEt, $OCH_2Ph$ and/or OPh. In yet another embodiment, one of $R^{14}$ and $R^{15}$ is $C_{1-10}$alkyl and the other of $R^{14}$ and $R^{15}$ is H. In another embodiment $R^{14}$ is $C_{1-10}$alkyl and $R^{15}$ is H. In another embodiment, $R^{14}$ is a straight chain $C_{1-10}$alkyl.

One example of a preferred compound of formula V is:

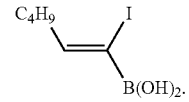

The compounds of formula V are either commercially available or are prepared using methods known in the art as described above for the compounds of formula II.

(c) Phenyl Boronic Acids

The present application further provides compounds of formula III:

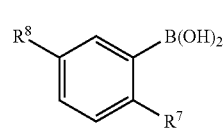

wherein $R^7$ is halo; and
$R^8$ is $OC_{1-6}$alkyl, $OC_{6-10}$aryl or $OC_{1-4}$alkylene$C_{6-10}$aryl. In one embodiment of the phenyl boronic acid of formula III, when $R^7$ is I, $R^8$ is not $OC_{1-4}$alkyl.

The phenyl boronic acids of formula III includes those compounds in which $R^7$ is I and $R^8$ is $OC_{5-6}$alkyl, $OC_{6-10}$aryl or $OC_{1-4}$alkylene$C_{6-10}$aryl. The phenyl boronic acids of formula III also include those compounds in which $R^8$ is OMe, OPh or $OCH_2Ph$.

The present disclosure includes compounds of formula III such as:

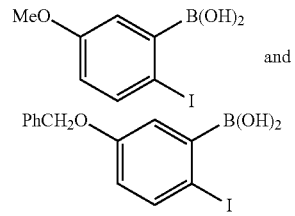

and

To gain a better understanding of the invention described herein, the following examples are set forth. It should be understood that these examples are for illustrative purposes only. Therefore, they should not limit the scope of this invention in any way.

EXAMPLES

Example 1

Preparation of (E)-2,3-Diiodobut-2-ene-1,4-Diol

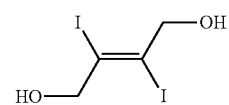

2-Butyne-1,4-diol (2.0 g, 23.2 mmol), iodine (6.0 g, 23.6 mmol), potassium iodide (8.0 g, 48.2 mmol) and water (70 mL) were heated to 70° C. on a steambath for an hour. The precipitate was separated, washed and crystallized from water to provide the desired iodinated product in 81% yield (6.4 g).

$^1$H-NMR (400 MHz, CD$_3$COCD$_3$, D$_2$O) δ 4.36 (s, 4H), 3.68 (s, 2H). $^{13}$C-NMR (100 MHz, CD$_3$COCD$_3$, D$_2$O) δ 96.5, 69.4.

Example 2

Preparation of 3,4-Diiodofuran

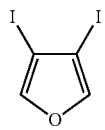

To a 2 L three-neck flask fitted with a stirrer, a water cooled condenser, and a 100 mL dropping funnel was added 2,3-diiodo-2-butene-1,4-diol (Example 1, 25 g, 73.5 mmol), N-methylpyrrolidinone (NMP) (300 mL), and hexanes (500 mL). The mixture was stirred vigorously at 85° C. To this solution was added a preheated (85° C.) solution of K$_2$Cr$_2$O$_7$ (21.6 g, 73.5 mmol) in H$_2$SO$_4$ (3 M, 90 mL) dropwise in portions (30 mL) over 1 h. The biphasic mixture was stirred at 85° C. for 5 h and then allowed to cool to room temperature. The hexane layer was decanted, and the remaining solvent was extracted once with hexanes (250 mL).

The hexane layers were combined, washed successively with water (2×120 mL), a saturated Na$_2$S$_2$O$_3$ solution (120 mL), and brine (120 mL), dried, passed over a short plug of silica gel, and concentrated to give the desired product in 7% yield (1.6 g) as a pale yellow liquid The characterization of the compound matched the previous report: C. C. Hughes, J. J. Kennedy-Smith, D. Trauner, Org. Lett. 2003, 5, 4113.

Example 3

Preparation of 4-Iodofuran-3-yl-3-Boronic Acid (Catalyst Ia)

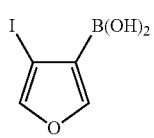

(Ia)

To a solution of 3,4-diiodofuran (Example 2, 1.27 g, 3.98 mmol) in 60 mL of a mixture of tetrahydrofuran (THF) and Et$_2$O (1:1) was added dropwise at 78° C., isopropylmagnesium chloride (2 M in THF, 4.37 mmol). After the mixture was stirred for 2 h at that temperature, B(O-iPr)$_3$ (6.91 mL, 11.9 mmol) was added. The solution was warmed to room temperature overnight; then a saturated solution of NH$_4$Cl was added, and the resulting mixture was stirred for 30 min at room temperature. The aqueous layer was extracted with Et$_2$O (40 mL, 3 times) and the ether extracts were dried over Na$_2$SO$_4$, filtered, concentrated and the crude product was purified by column chromatography (hexanes/ethyl acetate 3/1) to give the desired product in 54% yield (0.51 g).

Example 4

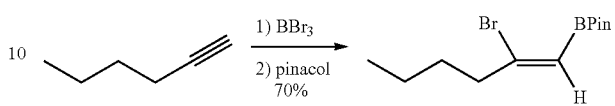

To a solution of 1-hexyne (1.64 g, 20 mmol) in dry CH$_2$Cl$_2$ (10 mL) was added BBr$_3$ (22 mL of a 1.0 M solution in heptanes, 22 mmol) at −78° C. After 1 h at −78° C., the reaction mixture was warmed to room temperature, kept at this temperature for 1 h, and added to a solution of pinacol (2.84 g, 24 mmol) in dry CH$_2$Cl$_2$ (20 mL) at −78° C. The resultant reaction mixture was warmed to room temperature, stirred for 1 h, washed with brine, and dried over Na$_2$SO$_4$. After evaporation of the solvent, the residue was purified by column chromatography (silica gel, 0%→2%→4% of EtOAc in hexane) to give the desired compound (Wang, C., Tobrman, T., Xu, Z., Negishi, E. Org. Lett. 2009, 11, 4092-4095) as a brown oil (2.27 g, 70%). $^1$H NMR (300 MHz, CDCl$_3$): δ=0.90 (t, J=7.3 Hz, 3H), 1.26-1.40 (m, 14H), 1.48-1.62 (m, 2H), 2.51 (dt, J=0.8, 7.4 Hz, 2H), 5.86 (t, J=0.9 Hz, 1H). $^{13}$C NMR (100 MHz, CDCl$_3$): δ=13.4, 21.2, 24.4, 29.7, 44.6, 83.2, 144.8. $^{11}$B NMR (128 MHz, CDCl$_3$): δ=29.3. HRMS (EI) for C$_{12}$H$_{22}$$^{11}$B$^{79}$BrO$_2$: calcd. 288.08963. found, 288.08937.

Example 5

Preparation of Catalyst IIa

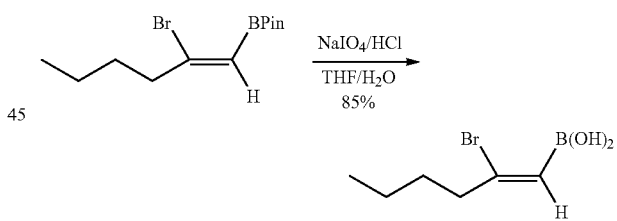

Boronic acid pinacol ester from Example 5 (2.31 g, 8 mmol) and sodium periodate (5.16 g, 24 mmol) were stirred in 65 mL of a 4:1 mixture of THF and water for 30 min, at which time aqueous hydrochloric acid (1N, 5.6 mL, 5.6 mmol) was added to the suspension. The reaction mixture was stirred at room temperature overnight (14 h), diluted with water (30 mL) and extracted with ethyl acetate (2×60 mL). The combined extracts were washed with water (2×30 mL) and brine (30 mL), dried over Na$_2$SO$_4$, filtered and concentrated in vacuo to give the desired boronic acid IIa (Tzschucke, C. C., Murphy, J. M., Hartwig, J. F. Org. Lett. 2007, 9, 761-764) (1.41 g, 6.8 mmol) as a yellow oil. $^1$H NMR (300 MHz, CDCl$_3$): δ=0.92 (t, J=7.3 Hz, 2H), 1.24-1.40 (m, 2H), 1.50-1.64 (m, 2H), 2.58 (dt, J=1.0, 7.3 Hz, 2H), 6.82 (t, J=1.0 Hz, 1H). $^{13}$C NMR (100 MHz, CDCl$_3$): δ=13.4, 21.1, 29.6, 44.6, 145.8. $^{11}$B (128 MHz, CDCl$_3$): δ=27.5. HRMS (EI) for C$_6$H$_{12}$O$_2$$^{11}$B$^{79}$Br: calcd, 206.01137. found, 206.01122.

Example 6

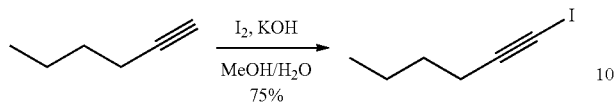

To a solution of 1-hexyne (2.46 g, 30 mmol) in methanol (30 mL) was added a solution of potassium hydroxide (4.2 g, 75 mmol, 2.5 eq) in water (6 mL) followed by iodine (10.2 g, 39 mmol, 1.3 eq). After being stirred at room temperature for 3 h, the mixture was diluted with water (30 mL) and the aqueous layer was extracted with ether (3×25 mL). The combined organic layers were dried over Na$_2$SO$_4$, and concentrated in vacuo to afford the desired compound (Denmark, S. E., Yang, S-M. Tetrahedron 2004, 60, 9695-9708; Denmark, S. E., Yang, S-M. J. Am. Chem. Soc. 2002, 124, 2102-2103) (4.68 g, 75%) as a yellow oil. $^1$H NMR (400 MHz, CDCl$_3$): δ=0.91 (t, J=7.2 Hz, 3H), 1.34-1.54 (m, 4H), 2.36 (t, J=7.1 Hz, 2H). $^{13}$C NMR (100 MHz, CDCl$_3$): δ=8.0, 13.2, 20.1, 21.5, 30.2, 94.4.

Example 7

Preparation of Catalyst IIb

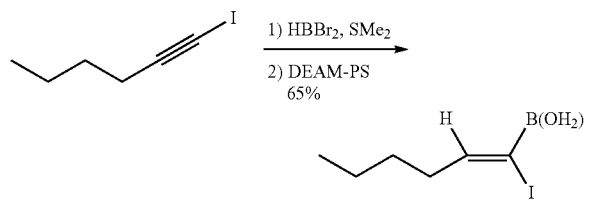

To a solution of the compound from Example 6 (624 mg, 3 mmol) in dry CH$_2$Cl$_2$ (5 mL) at 0° C. under Argon was added HBBr$_2$.SMe$_2$ (3.6 mL of 1.0 M solution in CH$_2$Cl$_2$, 36 mmol) and the reaction mixture was allowed to reach room temperature and stirred for 2 h. The reaction mixture was then poured into a mixture of ice (20 g) and NaOH (300 mg, 7.5 mmol) and stirred for 3 min. Ethyl acetate (20 mL) was added and the aqueous layer washed with EtOAc (2×10 mL). The organic layer was dried over Na$_2$SO$_4$, filtered and concentrated in vacuo. The resulting oil was dissolved in THF (20 mL) and added to N,N-diethanolaminomethyl polystyrene (DEAM-PS) resin (2.61 g, 3 mmol, 1 eq, loading: 1.15 mmol g$^{-1}$) in a polypropylene (pp) reaction vessel. The reaction suspension was shaken at room temperature for 1 h and the pp vessel was drained. The resin was then washed with dry THF (2×20 mL). The resin-bound boronic acid was cleaved by vortexing the resin with a mixture of THF/H$_2$O/Ac$_2$O (90/5/5) (20 mL) for 1 min at room temperature. The product-containing solution was drained and the resin was washed with THF/H$_2$O/Ac$_2$O (90/5/5) (3×20 mL). The filtrates were combined, concentrated under reduced pressure and dried under high vacuum overnight to afford the desired boronic acid catalyst IIb (Waas, J. R., Sidduri, A., Knochel P., Dow, W. H. Tet. Lett. 1992, 33, 3717-3720) as a yellow oil. $^1$H NMR (400 MHz, CDCl$_3$): δ=0.95 (t, J=7.2 Hz, 3H), 1.34-1.58 (m, 4H), 2.37 (dt, J=6.8, 7.0 Hz, 2H), 7.29 (t, J=6.8 Hz, 1H). $^{13}$C NMR (100 MHz, CDCl$_3$): δ=13.6, 22.1, 29.2, 38.1, 159.9. $^{11}$B NMR (128 MHz, CDCl$_3$): δ=26.2. HRMS (EI) for C$_6$H$_{12}$O$_2$$^{11}$BI: calcd. 253.99750. found, 253,99761.

Example 8

Preparation of Catalyst IIc

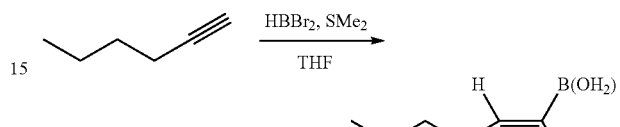

To a solution of 1-hexyne 246 mg, 3 mmol) in dry CH$_2$Cl$_2$ (5 mL) at 0° C. under Argon was added HBBr$_2$.SMe$_2$ (3.6 mL of 1.0 M solution in CH$_2$Cl$_2$, 36 mmol) and the reaction mixture was allowed to reach room temperature and stirred for 2 h. The reaction mixture was then poured into a mixture of ice (20 g) and NaOH (300 mg, 7.5 mmol) and stirred for 3 min. Ethyl acetate (20 mL) was added and the aqueous layer washed with EtOAc (2×10 mL). The organic layer was dried over Na$_2$SO$_4$, filtered and concentrated in vacuo to provide catalyst IIc. $^1$H NMR (300 MHz, CDCl$_3$): δ=0.92 (t, J=7.3 Hz, 3H), 1.24-1.52 (m, 4H), 2.18-2.28 (m, 2H), 5.54 (dt, J=1.5, 7.6 Hz, 1H), 6.97 (dt, J=6.5, 17.6 Hz, 1H). $^{13}$C NMR (100 MHz, CDCl$_3$): δ=13.5, 21.9, 30.0, 34.9, 157.3. $^{11}$B NMR (128 MHz, CDCl$_3$): δ=28.3.

Example 9

General Procedure for Halogenation of Arylboronic Acids

A solution of iodine in EtOH (4.72 mmol, 1.00 equiv, 0.30 M) was added dropwised to a mixture of arylboronic acid (4.72 mmol, 1.00 equiv) and silver (I) sulfate (2.36 mmol, 0.55 equiv) in EtOH (15 mL) at room temperature. After complete addition of iodine the reaction was stirred at room temperature until the iodine color completely disappeared. The reaction mixture was filtered through a pad of Celite® 545 using ethyl acetate. Water (50 mL) was added to the filtrate and the mixture was extracted with ethyl acetate (2×30 mL). The combined organic layers were washed with aqueous sodium sulfite, brine, dried over Na$_2$SO$_4$, filtered and concentrated. The residue was chromatographed on silica gel (hexane/ethyl acetate 3:1) to yield the pure desired product.

(a): Preparation of 2-Iodo-5-Methoxyphenyl Boronic Acid (IIIa)

The title compound was prepared using the general procedure for halogenation of arylboronic acids and isolated in 81% yield as a white solid. IR (Cast film, cm$^{-1}$) 3373, 1563, 1441, 1398, 1334, 1281, 1231, 1035, 810. $^1$H NMR (400 MHz, d-DMSO) δ: 8.22 (bs, 2H), 7.58 (d, 1H, J=8.6 Hz), 6.79 (d, 1H, J=3.2 Hz), 6.66 (dd, 1H, J=3.2 Hz, J=8.6 Hz), 3.71 (s, 3H). $^{13}$C NMR (100 MHz, CDCl$_3$) δ: 159.1, 139.2, 119.6, 116.9, 88.2, 55.8. HRMS (ESI) for C$_7$H$_8$ClIO$_3$: calcd. 312.93065. found, 312.92965.

(b) Preparation of 2-Iodo-5-Benzyloxyphenyl Boronic Acid (IIIa)

The title compound was prepared using the general procedure for halogenation of arylboronic acids and isolated in 88% yield as a white solid. IR (Cast film, cm$^{-1}$) 3332, 3059, 1582, 1493, 1472, 1460, 1338, 1278, 1167, 1137, 1000. $^1$H NMR (400 MHz, d-DMSO) δ: 8.26 (s, 2H), 7.58 (d, 1H, J=8.6 Hz), 7.35 (m, 5H), 6.88 (d, 1H, J=3.1 Hz), 6.74 (dd, 1H, J=3.2 Hz, J=8.7 Hz), 5.06 (s, 2H). $^{13}$C NMR (100 MHz, d-DMSO) δ: 158.2, 139.3, 137.6, 129.1, 128.5, 128.2, 120.7, 117.7, 88.5, 69.8. HRMS (ESI) for $C_{13}H_{12}BINaO_3$: calcd. 376.98188. found, 367.98168.

Example 10

Comparative Amidation Reactions Using Various Catalysts

General Amidation Reaction Conditions

Into a 25 mL round bottom flask equipped with a stir bar was added carboxylic acid (0.55 mmol, 1.1 equiv), boronic acid catalyst (0.05 mmol, 10 mol %) and 1 g of activated 4 Å molecular sieves (preactivation overnight in an oven at 250° C. or 2 h in a Kugelrohr apparatus at 250° C. under high vacuum). Solvent (5 mL) was added and the mixture was stirred for 10 min. Then, amine (0.5 mmol, 1 equiv) was added (for better, reproducible results, a gas tight 100 μl syringe was used). The resulting mixture was stirred at room temperature (24-25° C.). The reaction mixture was filtered through a pad of Celite® 545, the filtrate was washed with aqueous acidic solution (pH=4), aqueous basic solution (pH=10-11) and brine. The organic layer was collected, dried over anhydrous $Na_2SO_4$, filtered and evaporated to yield the title amide product.

Boronic acid catalyst Ia was subjected to a model amidation reaction with phenylacetic acid and pyrrolidine under the general amidation reaction conditions. In this event, catalyst Ia provided a quantitative yield of the desired amide product after 6 hours of reaction (Scheme 1).

Scheme 1

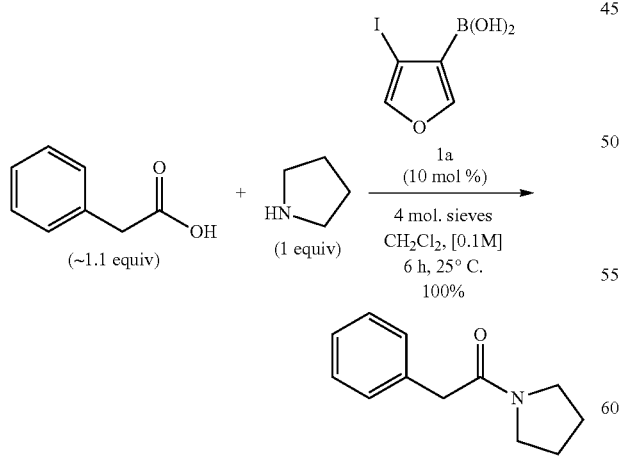

The use of 5-methoxy-2-iodophenylboronic acid (Ma) and 4-iodo-3-furanboronic acid (Ia) as catalysts under the general amidation reaction conditions in three hour long side-by-side reactions was investigated (see Scheme 2).

Scheme 2

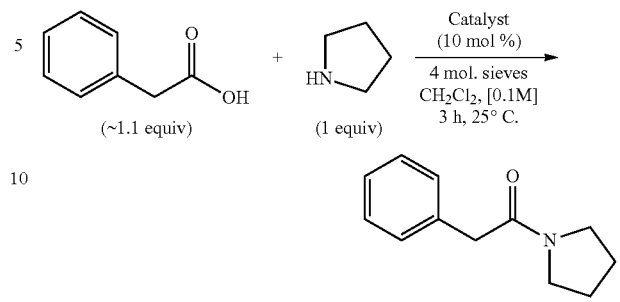

Catalysts

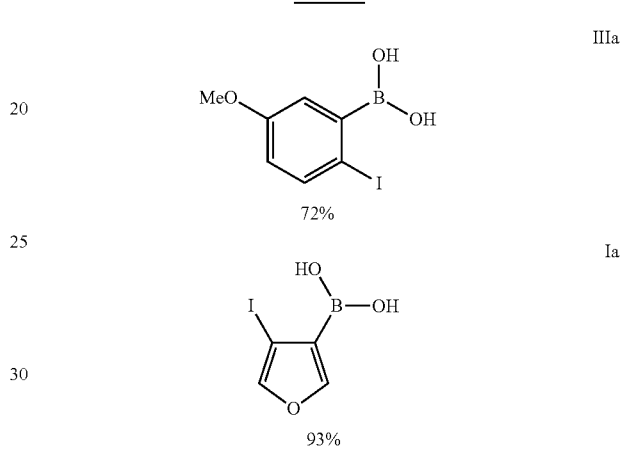

Catalyst Ia led to a relatively faster catalyzed amidation reaction providing a higher yield of one of the most demanding amidation reactions (tertiary amide) between phenylacetic acid and pyrrolidine. These catalysts' effect on the preparation of other aliphatic amides (Scheme 3) and α-substituted amides (Scheme 4) was significant, providing the desired products in short reaction times and higher yield (avoiding epimerization side reactions) than a related prior art catalyst. In reactions between aromatic carboxylic acids and α-amino acids catalyst Ia providing only low yields after 24 hours under the current reaction conditions.

Scheme 3

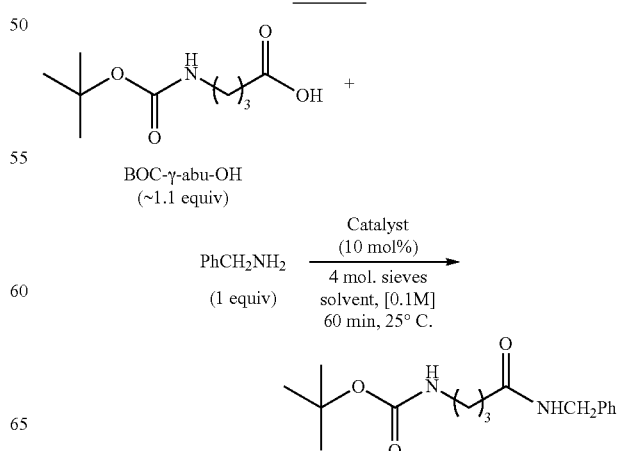

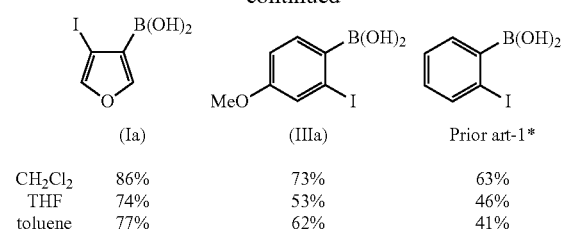

| | (Ia) | (IIIa) | Prior art-1* |
|---|---|---|---|
| CH$_2$Cl$_2$ | 86% | 73% | 63% |
| THF | 74% | 53% | 46% |
| toluene | 77% | 62% | 41% |

*Hall et al. PCT Patent Application Publication No. WO 2009/030022

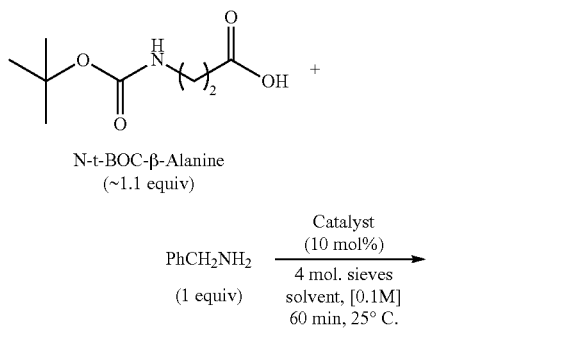

N-t-BOC-β-Alanine
(~1.1 equiv)

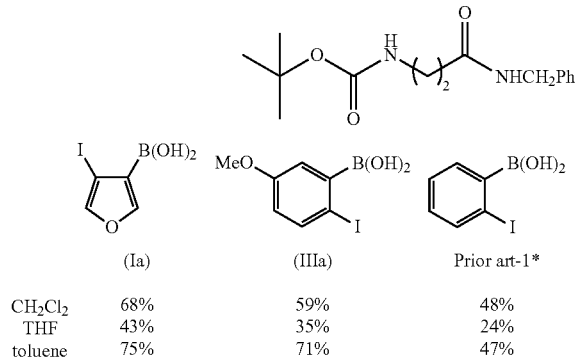

| | (Ia) | (IIIa) | Prior art-1* |
|---|---|---|---|
| CH$_2$Cl$_2$ | 68% | 59% | 48% |
| THF | 43% | 35% | 24% |
| toluene | 75% | 71% | 47% |

*Hall et al. PCT Patent Application Publication No. WO 2009/030022

To determine the relative rates of catalyzed direct amidation reactions using ortho-iodoboronic acid catalysts, a model reaction between ibuprofen and pyrrolidine was carried out and terminated after exactly 8.0 hours. The model amidation reaction gave 68% and 51% conversion in CH$_2$Cl$_2$ with (Ia) and (IIIa), respectively, compared to 43% conversion with a prior art catalyst (Scheme 4).

Scheme 4

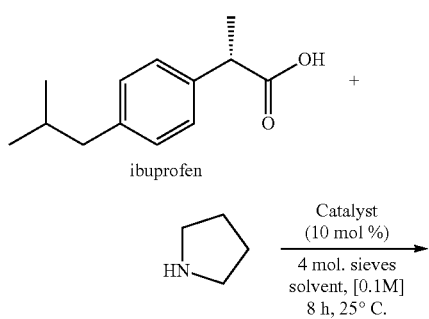

ibuprofen

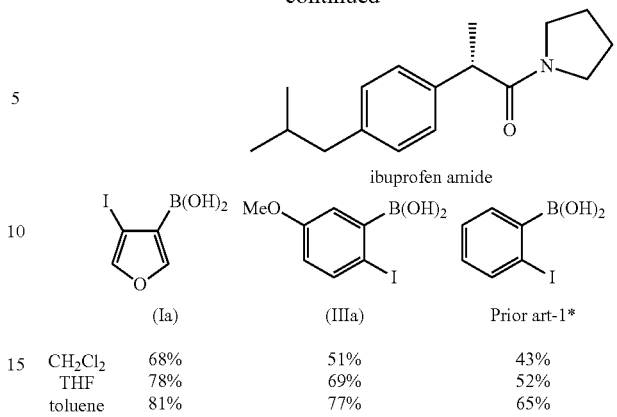

ibuprofen amide

| | (Ia) | (IIIa) | Prior art-1* |
|---|---|---|---|
| CH$_2$Cl$_2$ | 68% | 51% | 43% |
| THF | 78% | 69% | 52% |
| toluene | 81% | 77% | 65% |

*Hall et al. PCT Patent Application Publication No. WO 2009/030022

Example 11

Comparative Amidation Reactions

General Amidation Reaction Conditions

Into a 25 ml round bottom flask equipped with a stir bar was added phenyl acetic acid (0.075 g, 0.55 mmol, 1.1 eq), the catalyst (0.05 mmol, 10 mol %) and 1 g of activated 4 Å Molecular sieves (activated in a Kugelrohr apparatus under high vacuum at 250° C. overnight). Solvent (7 mL) was added and the mixture was stirred for 10 min. Then, pyrrolidine (42 μL, 0.5 mmol, 1 eq) was added (for better, reproducible results, a gas-tight 100 μl syringe was used). The resulting mixture was stirred for 2 h/48 h at room temperature (24-25° C.). The reaction mixture was filtered through a pad of Celite® 545, the filtrate was washed with aqueous acidic solution (pH=4), aqueous basic solution (pH=10-11) and brine. The organic layer was collected, dried over anhydrous Na$_2$SO$_4$ and evaporated to yield the title compound as a pure product.

Results for 2 h reaction time:

Scheme 5

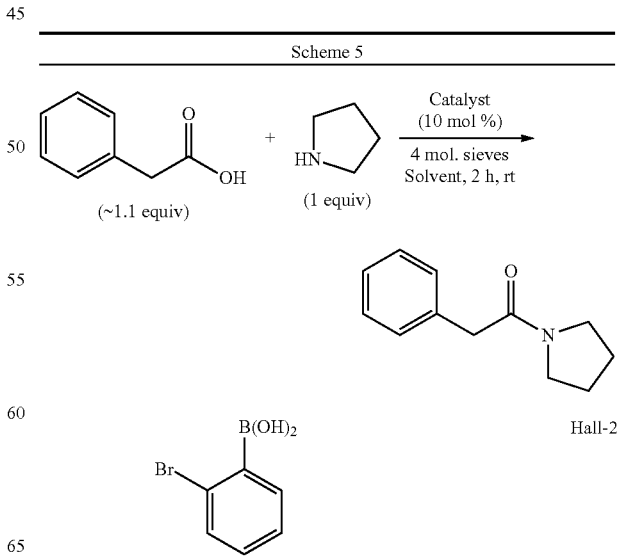

-continued

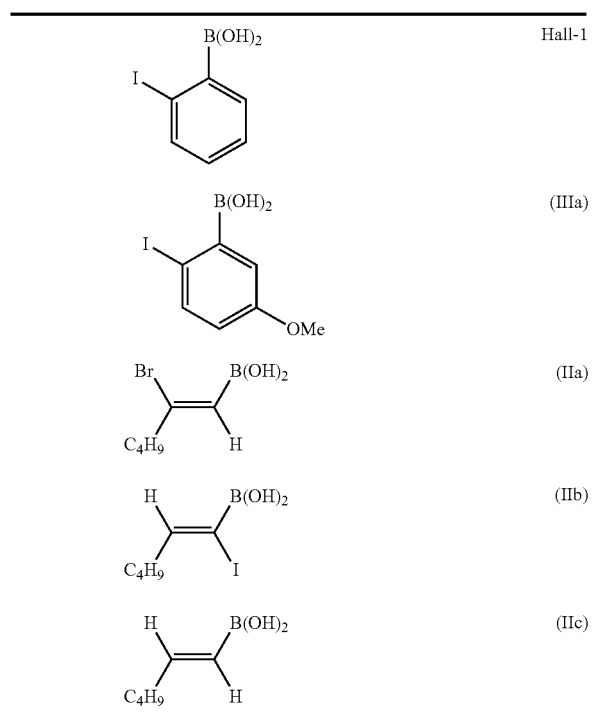

| Catalyst | Hall-2 | Hall-1 | IIIa | IIa | IIb | IIc |
|---|---|---|---|---|---|---|
| CH$_2$Cl$_2$ | 30% | 40% | 65% | 20% | 50% | <5% |
| THF | <5% | <5% | 15% | <5% | 10% | <5% |
| Toluene | <5% | 5% | 10% | <5% | 8% | <5% |

*The first two compounds are as described in Hall et al. PCT Patent Application Publication No. WO 2009/030022

Results for 48 h reaction time:

Scheme 6

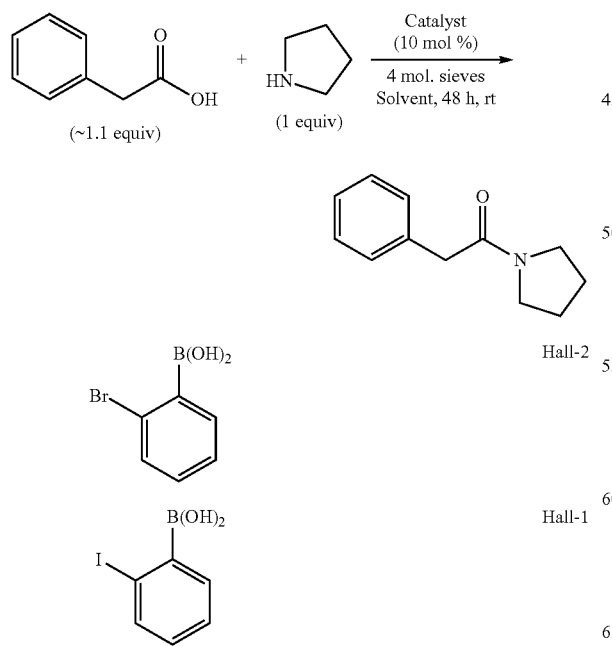

-continued

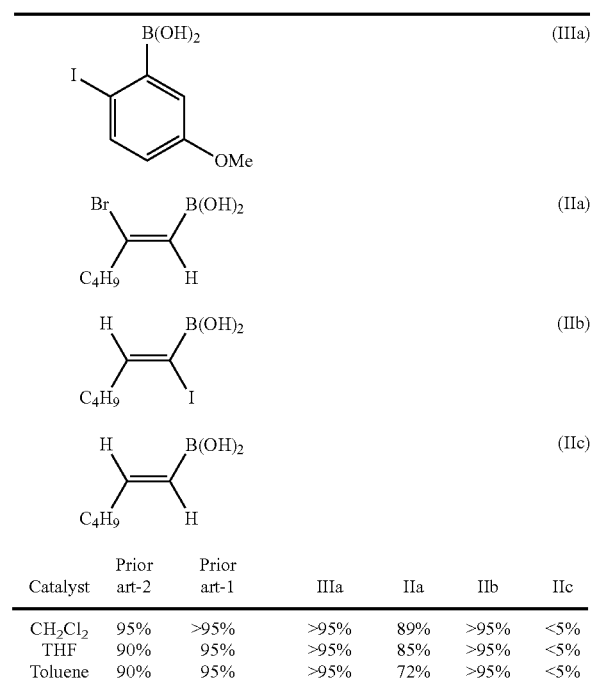

| Catalyst | Prior art-2 | Prior art-1 | IIIa | IIa | IIb | IIc |
|---|---|---|---|---|---|---|
| CH$_2$Cl$_2$ | 95% | >95% | >95% | 89% | >95% | <5% |
| THF | 90% | 95% | >95% | 85% | >95% | <5% |
| Toluene | 90% | 95% | >95% | 72% | >95% | <5% |

* The first two compounds are as described in Hall et al. PCT Patent Application Publication No. WO 2009/030022

Example 12

Examination of the Effect of Electron Donating Groups Para to Halo Group in 2-Halophenyl Boronic Acid Catalysts A variety of 2-iodophenyl boronic acid catalysts further substituted with electron donating groups were prepared and used in amidation reactions using the conditions set out in Scheme 7. Their activity was also compared with the unsubstituted 2-iodophenyl boronic acid catalysts.

Scheme 7

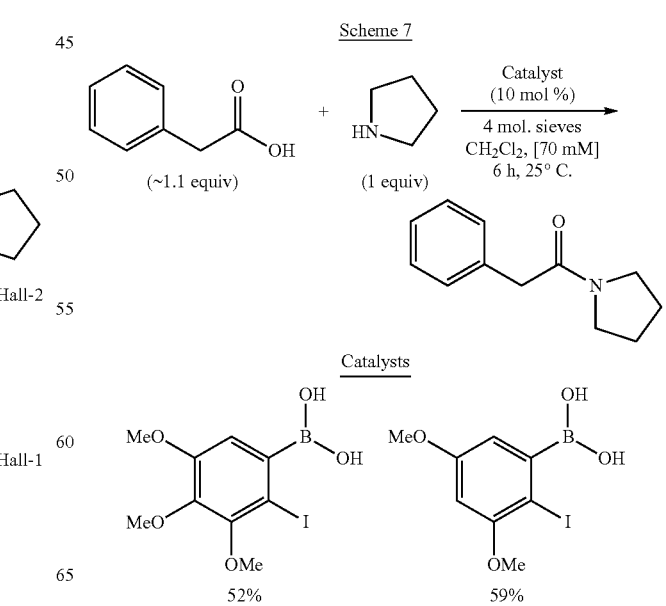

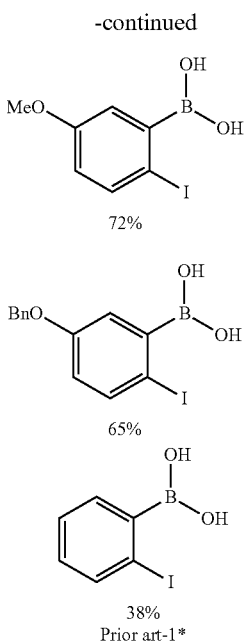

(IIIa) 72%

(IIIb) 65%

38%
Prior art-1*

Placement of an electron donating substituent at the para-position to the iodo group on the aromatic ring rendered significant effects. For example, introduction of a methoxy group at position 5 of the aromatic ring, as in IIIa, led to a significant increase in observed amide yields (72% compared to 38% for catalyst Prior art-1), while having a benzyloxy group, as in IIIb, led to 65% of the desired amide product.

Example 13

Preparation of N-Phthalimide-Protected Amino Acids

These compounds were prepared following the procedure of Pinter, A. and Habberhauer, G. *Eur. J. Org. Chem.* 2008, 2375-2387. In a three-necked round-bottom flask were placed the amino-acid (30.0 mmol), phthalic anhydride (4.44 g, 30.0 mmol, 1 eq), triethylamine (0.303 g, 3.0 mmol, 0.1 eq) and toluene (20 mL). The flask was equipped with a stirring bar, a Dean-Stark trap and a reflux condenser. The mixture was heated to reflux temperature and stirred for further 6 h with azeotropic removal of water. The solvent was then removed in a rotary evaporator. The resulting white solid was taken up in water (45 mL) and the mixture was acidified by adding concentrated hydrochloric acid (0.6 mL, 6.6 mmol). The product was collected by filtration, washed with water (2×5 mL) and dried to yield the carboxylic acid as a white powder.

(a) N-Phthalimidoglycine
$^1$H NMR (300 MHz, CDCl$_3$): δ=3.94 (s, 2H), 7.34-7.40 (m, 2H), 7.42-7.48 (m, 2H).

(b) N-Phthalimidoalanine
$^1$H NMR (300 MHz, CDCl$_3$): δ=1.54 (d, J=7.3 Hz, 3H), 4.85 (q, J=7.3 Hz, 1H), 7.83-7.92 (m, 4H).

(c) N-Phthalimidoleucine
$^1$H NMR (300 MHz, CDCl$_3$): δ=0.84 (t, J=5.4 Hz, 6H), 1.34-1.50 (m, 1H), 1.76-1.90 (m, 1H), 2.08-2.24 (m, 1H), 4.74 (dd, J=4.0, 11.1 Hz, 1H), 7.84-7.92 (m, 4H).

Example 14

T-BOC and Methoxycarbonyl Amino Acid Esters

These compounds were prepared from corresponding commercially available hydrochloric salt by basic treatment in presence of aqueous solution of NaOH (1 eq). The aqueous layers were extracted with DCM (4 times) and the resulting organic layers were dried over Na$_2$SO$_4$ and concentrated under vacuum to give the resulting products as colorless oils.

(a) t-BOC-Glycine
$^1$H NMR (300 MHz, CDCl$_3$): δ=1.43 (s, 9H), 3.27 (s, 2H).

(b) t-BOC-Alanine
$^1$H NMR (300 MHz, CDCl$_3$): δ=1.25 (d, J=7.0 Hz, 3H), 1.43 (s, 9H), 3.38 (q, J=7.0 Hz).

(c) t-BOC-Leucine
$^1$H NMR (300 MHz, CDCl$_3$): δ=0.92 (t, J=6.9 Hz, 6H), 1.30-1.58 (m, 11H), 1.68-1.82 (m, 1H), 3.32 (dd, J=5.9, 8.4 Hz, 1H).

(d) Methoxycarbonylleucine
$^1$H NMR (300 MHz, CDCl$_3$): δ=0.9 (dd, J=5.2, 6.6 Hz, 6H), 1.33-1.58 (m, 4H), 1.65-1.84 (m, 1H), 3.60 (dd, J=5.6, 8.7 Hz, 1H), 3.68 (s, 3H).

Example 15

Amino Acid Amidation Reactions

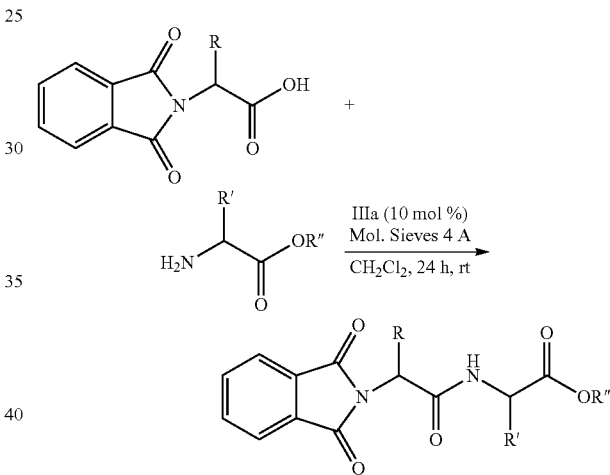

Into a 25 ml round bottom flask equipped with a stir bar was added carboxylic acid (0.55 mmol, 1.1 eq), the catalyst (0.05 mmol, 10 mol %) and 1 g of activated 4 Å Molecular sieves (activated on Kugel Rohr under high vacuum at 250° C. overnight). Solvent (7 mL) was added and the mixture was stirred for 10 min. Then, amine (0.5 mmol, 1 eq) was added (for better, reproducible results, a gas tight 100 μl syringe was used). The resulting mixture was stirred for 2 h to 48 h at room temperature (24-25° C.). The reaction mixture was filtered through a pad of Celite® 545, the filtrate was washed with aqueous acidic solution (pH=4), aqueous basic solution (pH=10-11) and brine. The organic layer was collected, dried over anhydrous Na$_2$SO$_4$ and evaporated to yield the desired compound as a pure product.

(a) R=R'=H, R"=t-Bu
$^1$H NMR (300 MHz, CDCl$_3$): δ=1.43 (s, 9H), 3.92 (d, J=5.0 Hz, 2H), 4.39 (s, 2H), 6.52 (t, J=5.0 Hz, 1H), 7.68-7.74 (m, 2H), 7.82-7.88 (m, 2H).

(b) R=H, R'=Me, R"=t-Bu
$^1$H NMR (300 MHz, CDCl$_3$): δ=1.15 (d, J=7.1 Hz, 3H) 1.47 (s, 9H), 3.85-3.90 (m, 1H), 4.39 (s, 2H), 6.58 (t, J=5.0 Hz, 1H), 7.65-7.75 (m, 2H), 7.83-7.91 (m, 2H).

(c) R=H, R'=i-Bu, R"=t-Bu $^1$H NMR (300 MHz, CDCl$_3$): δ=0.82 (t, J=5.0 Hz, 6H), 1.30-1.44 (m, 1H), 1.45 (s, 9H), 1.70-1.85 (m, 1H), 2.02-2.18 (m, 1H), 3.88 (d, J=5.0 Hz, 2H), 5.18-5.25 (m, 1H), 6.22 (bs, 1H), 7.64-7.70 (m, 2H), 7.72-7.78 (m, 2H).

(d) R═H, R'=Me, R"=t-Bu $^1$H NMR (300 MHz, CDCl$_3$): δ=0.96 (s, 9H), 1.15 (d, J=7.3 Hz, 3H), 3.27 (d, J=4.7 Hz, 1H), 4.26 (s, 2H), 6.08 (m, 1H), 7.22-7.34 (m, 4H).

(e) R═H, R'=i-Bu, R"=Me $^1$H NMR (300 MHz, CDCl$_3$): δ=0.92 (d, J=5.3 Hz, 6H), 1.50-1.70 (m, 3H), 3.72 (s, 3H), 4.32-4.46 (m, 2H), 4.60-4.70 (m, 1H), 6.26 (d, J=8.1 Hz, 1H), 7.71-7.76 (m, 2H), 7.86-7.90 (m, 2H).

Yields

| Acid | Amine | | | |
|---|---|---|---|---|
| | H$_2$NGlyOtBu | H$_2$NAlaOtBu | H$_2$NLeuOtBu | H$_2$NLeuOMe |
| PhtGlyOH | 28% | 10% | <5% | 10% |
| PhtAlaOH | 12% | <5% | <5% | <5% |
| PhtLeuOH | 6% | <5% | <5% | <5% |

Example 16

Catalyst Screening

Catalysts were screened in accordance with the general methods as described, in accordance with the scheme depicted below.

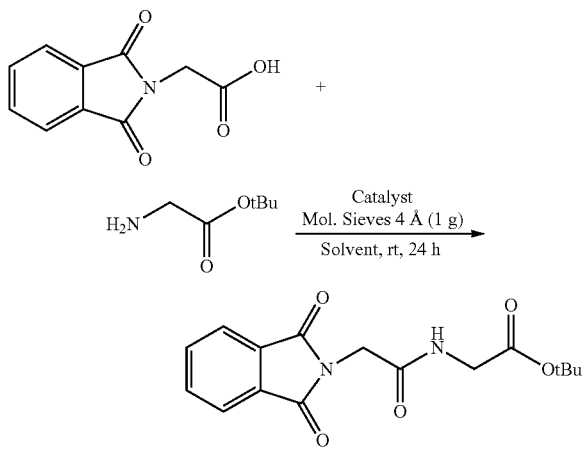

| Catalyst structure | Catalyst loading | Yield |
|---|---|---|
| (IIIa) | 10% | 28% |
| (IIIa) | 20% | 55% |
| (IIb) | 20% | 35% |

Example 17

Alternative preparation of 4-iodofuran-3-boronic acid catalyst

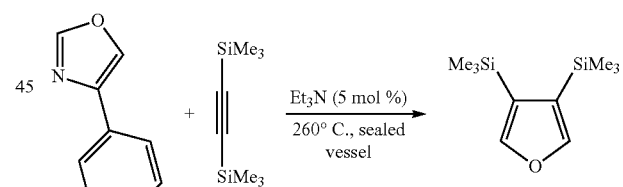

To a 40 mL stainless steel reaction vessel (Paar high pressure systems) was placed the 4-phenyloxazole (6.50 g, 44.8 mmol), the bis(trimethylsilyl)acetylene (7.27 g, 42.6 mmol), and triethylamine (0.040 mL). A magnetic stir-bar was added and the vessel was sealed. The mixture was heated to 260° C. with stirring. Internal pressures reached 3.5-5 bar. After heating for 16 h, the vessel was cooled to room temperature and the resulting black solution was eluted through a plug of silica gel (hexanes eluent, ca. 800 mL). The colorless eluent was evaporated under reduced pressure to give a pale yellow oil that consisted primarily of 3,4-bis(trimethylsilyl)furan (8.71 g, 96%). A small amount of the 2,4-bis(trimethylsilyl)furan (7-15% by integration of $^1$H NMR signals) remained as an inseparable impurity. $^1$H NMR: δ 7.40 (s, 1H), 0.29 (s, 9H). Ref.: Ho, M. S., Wong, H. N. C., *J. Chem. Soc., Chem. Commun.*, 1989, 1238-1239.

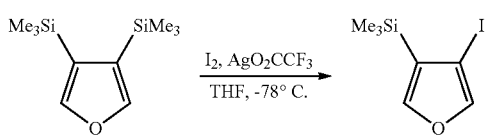

To a 250 mL round-bottomed flask equipped with a magnetic stir-bar was placed the 3,4-bis(trimethylsilyl)furan (2.00 g, 9.41 mmol) as a solution in THF (138 mL). Silver trifluoroacetate (4.16 g, 18.8 mmol) was added and the mixture was stirred for 5 min at room temperature until the silver salt dissolved. The resulting colorless solution was cooled to −78° C. and I$_2$ was then added as a solution in THF (50 mL) over 10 min. The mixture was stirred at −78° C. for 3 h after which time it was warmed to room temperature diluted with Et$_2$O (200 mL) and then filtered through a cake of celite. The resulting brown solution was then washed with 50% aqueous Na$_2$S$_2$O$_3$ (2×80 mL) followed by saturated aqueous NaHCO$_3$ (50 mL), and then brine (50 mL). The organic layer was then dried over Na$_2$SO$_4$. Evaporation of the solvent in vacuo gave a yellow oil that was eluted through a plug of silica gel (hexanes, ca. 400 mL eluent) to give a colorless solution. Evaporation of the solvent gave (4-iodofuran-3-yl)trimethylsilane as a pale pink oil (2.20 g, 87%). $^1$H NMR: δ 7.49 (d, 1H, J=1.5 Hz), 7.22 (d, 1H, J=1.5 Hz), 0.30 (s, 9H). Ref.: Song, Z. Z., Wong, H. N. C. Liebigs Ann. Chem. 1994, 29-34.

General reaction conditions were carried out in accordance with the general procedure as follows, and depicted in the reaction scheme below. The carboxylic acid (0.55 mmol, 1.1 equiv), boronic acid (0.05 mmol, 10 mol %) and the amine (0.5 mmol, 1 equiv) were stirred at room temperature (24-25° C.) for 2.5 h in 7 mL of solvent containing powdered activated 4 Å mol. sieves (1 g).

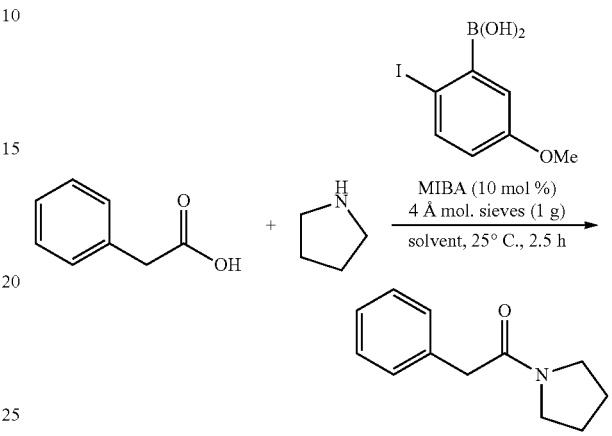

The percentage yields for each solvent are shown in FIG. 1, and in the Table shown below.

| Solvent | DCM | THF | Tol | MeNO$_2$ | Me—THF | CPME | MTBE | Chlorobenzene | 1,2-DCE |
|---|---|---|---|---|---|---|---|---|---|
| Yield (%) | 50 | 2 | 52 | 11 | 32 | 38 | 26 | 53 | 31 |

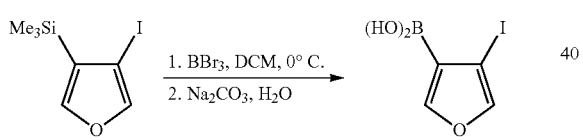

To a 100 mL round-bottomed flask equipped with a magnetic stir-bar was placed the (4-iodofuran-3-yl)trimethylsilane (500 mg, 1.88 mmol) as a solution in DCM (23 mL). The mixture was cooled to 0° C. and BBr$_3$ (2.25 mL of a 1.0 M solution in DCM) was added rapidly and the mixture turned dark red. The mixture was stirred at 0° C. for 10 min and then cannulated into a 1 M aqueous solution of Na$_2$CO$_3$ (30 mL). The organic layer was removed and set aside. The aqueous was acidified to pH 6 using ~5-6 mL of 6 M aqueous HCl, and extracted with EtOAc (3×20 mL). This extract was washed with brine (10 mL) and then dried over Na$_2$SO$_4$. Evaporation of the solid gave the boronic acid as a white solid (220 mg, 49%).

Example 18

Solvent Screening

The solvents screened for use with the present methods include dichloromethane (DCM), tetrahydrofuran (THF), toluene, nitromethane, methyl-tetrahydrofuran (Me-THF), cyclopentylmethyl ether (CPME), tert-butylmethyl ether (TBME), chlorobenzene and 1,2-dichloroethane (1,2-DME).

Example 19

Organocatalytic Amidations

General Procedure

Boronic acid catalysts as presently described were tested in an amidation reaction with a variety of carboxylic acid and amine starting materials to give a variety of amide products were carried out in accordance with the following general scheme:

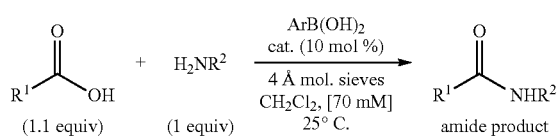

The general reaction conditions were as follows. The carboxylic acid (0.55 mmol, 1.1 equiv), boronic acid (0.05 mmol, 10 mol %) and the amine (0.5 mmol, 1 equiv) were stirred at room temperature (25° C.) in 7 mL of solvent containing powdered activated 4 Å mol. sieves (1 g). For each set of starting materials, two boronic acid catalysts were tested in the above reaction.

1
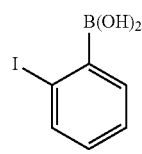
2
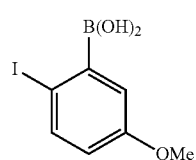 [SMILES: COc1ccc(I)c(B(O)O)c1]
Reaction yields are displayed for each catalyst under each amide product listed below as follows: Yield using cat. 1/Yield using cat. 2 (reaction time)
(a)
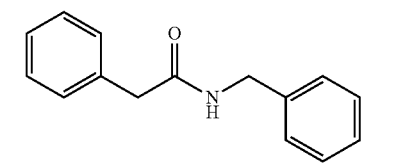 [SMILES: O=C(Cc1ccccc1)NCc1ccccc1]
71/98 (2 h)
(b)
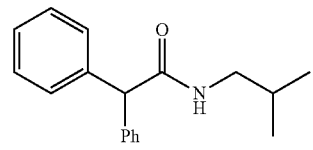 [SMILES: CC(C)CNC(=O)C(c1ccccc1)c1ccccc1]
44/58 (6 h)
(c)
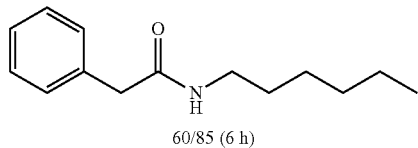
60/85 (6 h)
(d)
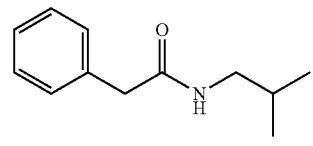
68/90 (2 h)
(e)
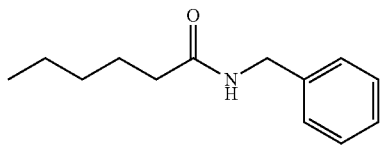
80/92 (6 h)
(f)
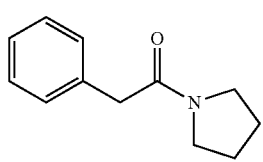 [SMILES: O=C(Cc1ccccc1)N1CCCC1]
66/91 (6 h)
(g)
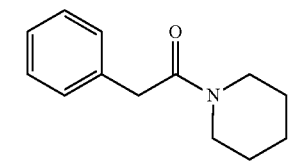 [SMILES: O=C(Cc1ccccc1)N1CCCCC1]
55/70 (48 h)
(h)
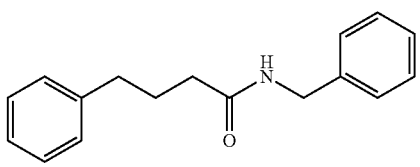 [SMILES: O=C(CCCc1ccccc1)NCc1ccccc1]
85/95 (2 h)
(i)
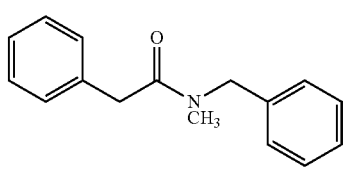
0/0 (48 h)
(j)
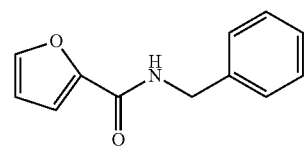 [SMILES: O=C(NCc1ccccc1)c1ccco1]
38/53 (48 h) (with 20 mol % cat. in DCM at 50° C.)
(k)
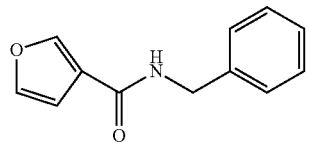 [SMILES: O=C(NCc1ccccc1)c1ccoc1]
32/44 (48 h) (with 20 mol % cat. in DCM at 50° C.)
(l)
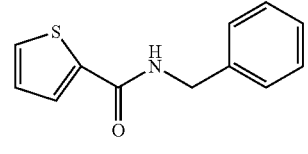
51/73 (48 h) (with 20 mol % cat. in DCM at 50° C.)
(m)
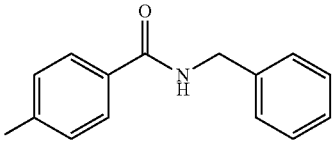
22/30 (48 h) (with 20 mol % cat. in toluene at 50° C.)
(n)
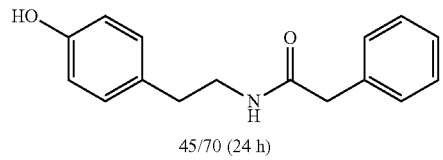
45/70 (24 h)

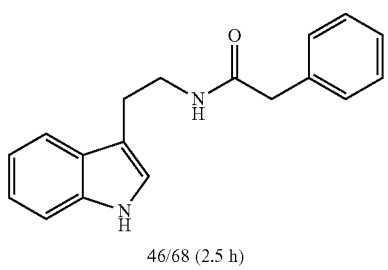

46/68 (2.5 h)

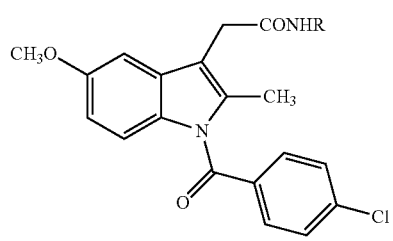

(i) R = (CH$_3$)$_2$CHCH$_2$ 50/65 (6 h)
(ii) R = PhCH$_2$ 62/85 (2 h)

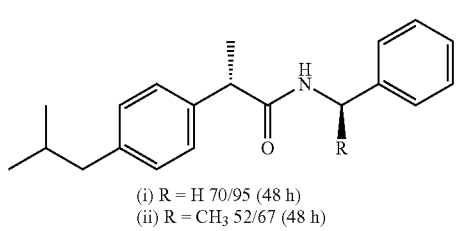

(i) R = H 70/95 (48 h)
(ii) R = CH$_3$ 52/67 (48 h)

Organocatalytic Amidations and Characterization of Compounds (a) N-benzyl-2-phenyl-acetamide

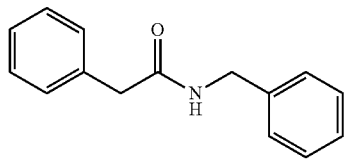

Into a 25 mL round bottom flask equipped with a stir bar was added phenylacetic acid (0.075 g, 0.55 mmol, 1.1 equiv), (2-iodo-5-methoxyphenyl)boronic acid (13.9 mg, 0.05 mmol, 10 mol %) and 1 g of activated 4 Å Molecular Sieves. Dichloromethane (7 mL) was added and the mixture was stirred for 10 min. Then, benzylamine (55 pit, 0.5 mmol, 1 equiv) was added (in order to get reproducible results, it is necessary to use a gas tight 100 µL syringe). The resulting mixture was stirred for 2 h at room temperature (24-25° C.). The reaction mixture was filtered through a pad of Celite® 545, the filtrate was washed with aqueous acidic solution (pH=4), aqueous basic solution (pH=10-11) and brine. The organic layer was collected, dried over anhydrous Na$_2$SO$_4$ and evaporated to yield the title compound (71% using 1, 98% using 2) as a pure product. The catalyst can be recuperated in up to 80% yield by acidification of the aqueous basic solution to pH 7 and extraction with EtOAc.

The characterization of the compound matched previous reports: Chan, W.-K., Ho, C.-M., Wong, M.-K., Che, C.-M. J. Am. Chem. Soc. 2006, 128, 14796-14797; Dittmer, D. C., Li, Q., Avilov, D. V. J. Org. Chem. 2005, 70, 4682-4686; Chen, Z.-W., Jiang, H.-F., Pan, X.-Y., He, Z.-J. Tetrahedron 2011, 67, 5920-5927.

(b) N-(2-methylpropyl)-2,2-diphenylacetamide

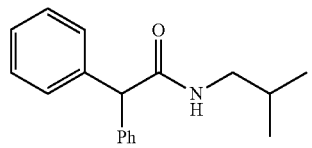

The title compound was prepared using the general procedure for the organocatalytic amidations (44% yield using 1, 58% using 2 after 6 h). $^1$H-NMR (300 MHz, CDCl$_3$) δ 7.40-7.20 (m, 10H), 5.96 (br s, 1H), 4.97 (s, 1H), 3.09 (dd, J=6.1 Hz, J=6.7 Hz, 2H), 1.73 (sept, J=6.6 Hz, 1H), 0.83 (d, J=6.7 Hz, 6H). $^{13}$C-NMR (125 MHz, CDCl$_3$) δ 172.0, 139.7, 128.9, 128.7, 127.2, 59.2, 47.1, 28.4, 20.0. IR (Microscope cm$^{-1}$) 3265, 1640. HRMS (ESI) for C$_{18}$H$_{21}$NONa: calcd. 290.1515. found 290.1510.

(c) N-hexyl-2-phenylacetamide

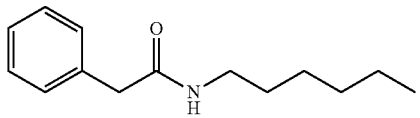

The title compound was prepared using the general procedure for the organocatalytic amidations (60% yield using 1 and 85% yield using 2 after 6 h). The characterization of the compound matched previous reports: Chan, W.-K., Ho, C.-M., Wong, M.-K., Che, C.-M. J. Am. Chem. Soc. 2006, 128, 14796-14797; Lee, H.-L., Aube, J. Tetrahedron 2007, 63, 9007-9015; Dam, J. H., Osztrovszky, G., Nordstroem, L. U., Madsen, R. Chem. Eur. J. 2010, 16, 6820-6827.

(d) N-(2-methoxypropyl)-2-phenylacetamide

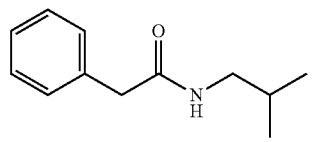

The title compound was prepared using the general procedure for the organocatalytic amidations (68% yield using 1 and 90% yield using 2 after 2 h). $^1$H-NMR (300 MHz, CDCl$_3$) δ 7.30-7.20 (m, 5H), 5.98 (br s, 1H), 3.52 (s, 2H), 2.99 (dd, J=6.1 Hz, J=6.8 Hz, 2H), 1.66 (sept, J=6.7 Hz, 1H), 0.78 (d, J=6.7 Hz, 6H). $^{13}$C-NMR (125 MHz, CDCl$_3$) δ 171.1, 135.3, 129.3, 128.8, 127.1, 46.9, 43.7, 28.4, 20.0. IR (Microscope cm$^{-1}$) 3278, 1643. HRMS (ESI) for $C_{12}H_{17}NONa$: calcd. 214.1202. found 214.1197.

(e) N-benzylhexanamide

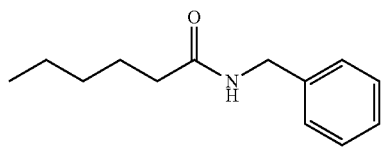

The title compound was prepared using the general procedure for the organocatalytic amidations (80% yield using 1 and 92% yield using 2 after 6 h). The characterization of the compound matched previous reports: Nordstrom, L. U., Vogt, H., Madsen, R. J. Am. Chem. Soc. 2008, 130, 17672-17673; Ghosh, S. C., Muthaiah, S., Zhang, Y., Xu, X., Hong, S. H. Adv. Synth. Cat. 2009, 351, 2643-2649; Dam, J. H., Osztrovszky, G., Nordstroem, L. U., Madsen, R. Chem. Eur. J. 2010, 16, 6820-6827.

(f) 2-phenyl-1-(pyrrolidin-1-yl)ethanone

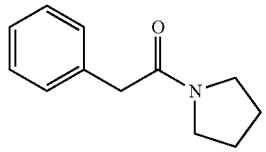

The title compound was prepared using the general procedure for the organocatalytic amidations (66% yield using 1 and 91% yield using 2 after 6 h). The characterization of the compound matched previous reports: Nelson, P., Pelter, A. J. Chem. Soc. 1965, 514-5144; Chen, Z.-W., Jiang, H.-F., Pan, X.-Y., He, Z.-J. Tetrahedron 2011, 67, 5920-5927; Pintori, D. G., Greaney, M. F. Org. Lett. 2011, 5713-5715.

(g) 2-phenyl-1-(piperidin-1-yl)ethanone

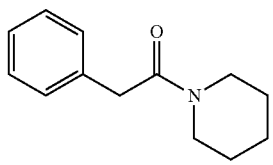

The title compound was prepared using the general procedure for the organocatalytic amidations (55% yield using 1 and 70% yield using 2 after 48 h). The characterization of the compound matched previous reports: Ghosh, S. C., Hong, S. H. Eur. J. Org. Chem. 2010, 4266-4270; Chiba, S., Zhang, L., Sanjaya, S., Ang, G. Y. Tetrahedron 2010, 66, 5692-5700; Schley, N., Dobereiner, G. E., Crabtree, R. H. Organometallics 2011, 30, 4174-4179.

(h) N-benzyl-4-phenylbutanamide

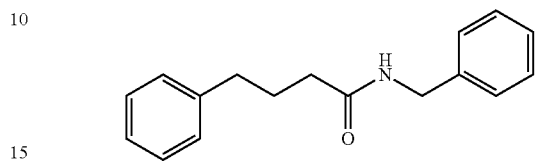

The title compound was prepared using the general procedure for the organocatalytic amidations (85% yield using 1 and 95% yield using 2 after 2 h). The characterization of the compound matched previous reports: Bejot, R., Anjaiah, S., Falck, J. R., Mioskowski, C. Eur. J. Org. Chem. 2007, 101-107; Maki, T., Ishihara, K., Yamamoto, H. Org. Lett. 2006, 8, 1431-1434.

(j) N-benzylfuran-2-carboxamide

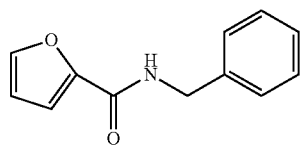

The title compound was prepared using the general procedure for the organocatalytic amidations (38% yield using 20 mol % of 1 and 53% yield using 20 mol % of 2 at 50° C. in DCM after 48 h). The characterization of the compound matched previous reports: Chen, C., Zhang, Y., Hong, H. J. Org. Chem. 2011, 76, 10005-10010; Laidaoui, N., Roger, J., Miloudi, A., El Abed, D., Doucet, H. Eur. J. Org. Chem. 2011, 4373-4385.

(k) N-benzylfuran-3-carboxamide

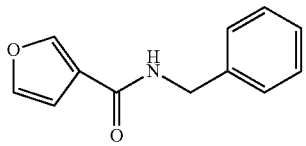

The title compound was prepared using the general procedure for the organocatalytic amidations (32% yield using 20 mol % of 1 and 44% yield using 20 mol % of 2 at 50° C. in DCM after 48 h). The characterization of the compound matched previous reports: Zanatta, N., Faoro, D., Silva, S. C., (l) N-benzylthiophene-2-carboxamide

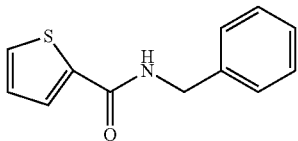 [SMILES: O=C(NCc1ccccc1)c1cccs1]

The title compound was prepared using the general procedure for the organocatalytic amidations (51% yield using 20 mol % of 1 and 73% yield using 20 mol % of 2 at 50° C. in DCM after 48 h). The characterization of the compound matched previous reports: Cui, X., Zhang, Y., Shi, F., Deng, Y. Chem. Eur. J. 2011, 17, 1021-1028; De Sarkar, S., Studer, A. Org. Lett. 2010, 12, 1992-1995; Laidaoui, N., Roger, J., Miloudi, A., El Abed, D., Doucet, H. Eur. J. Org. Chem. 2011, 4373-4385.

(m) N-benzyl-4-iodobenzamide

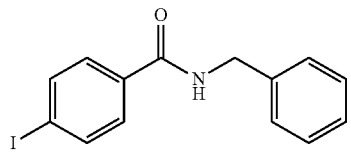 [SMILES: O=C(NCc1ccccc1)c1ccc(I)cc1]

The title compound was prepared using the general procedure for the organocatalytic amidations (22% yield using 20 mol % of 1 and 30% yield using 20 mol % of 2 at 50° C. in toluene after 48 h). The characterization of the compound matched previous reports: Klapars, A., Antilla, J. C., Huang, X., Buchwald, S. L. J. Am. Chem. Soc. 2001, 12, 7727-7729.

(n) N-[2-(4-hydroxyphenyl)ethyl]-2-phenylacetamide

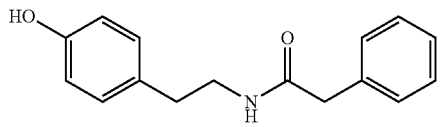 [SMILES: O=C(Cc1ccccc1)NCCc1ccc(O)cc1]

The title compound was prepared using the general procedure for the organocatalytic amidations (45% yield using 1 and 70% yield using 2 after 24 h). The characterization of the compound matched previous reports: Mahindroo, N., Connelly, M. C., Punchichewa, C., Kimura, H., Smeltzer, M. P., Wu, S., Fuji, N. J. Med. Chem. 2009, 52, 4277-4287; Boero-eczky, K., Laatsch, H., Wagner-Doebler, I., Stritzke, K., Schulz, S. Chem. Biodiv. 2006, 3, 622-634.

(o) N-[2-(1H-indol-3-yl)ethyl]-2-phenylacetamide

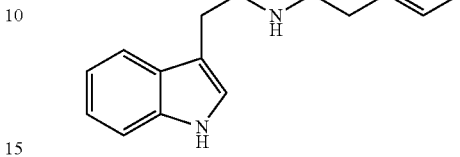

The title compound was prepared using the general procedure for the organocatalytic amidations (46% yield using 1 and 68% yield using 2 after 2.5 h). The characterization of the compound matched previous reports: Feldman, K. S., Vidulova, D. B. Org. Lett. 2004, 6, 1869-1871; Feldman, K. S., Vidulova, D. B., Karatjas, A. G. J. Org. Chem. 2005, 70, 6429-6440; Katritzky, A. R. J. Chem. Soc. 1955, 2586-2593.

(p (i)) 2-[1-(4-chlorobenzoyl)-5-methoxy-2-methyl-1H-indol-3-yl]-N-(2-methylpropyl)acetamide

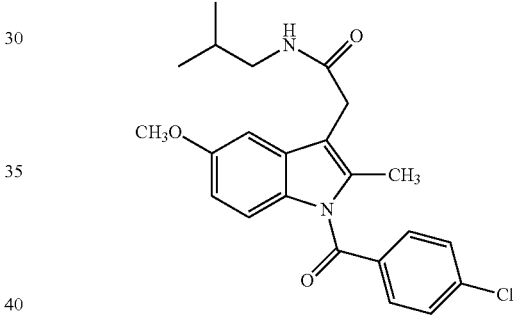

The title compound was prepared using the general procedure for the organocatalytic amidations (50% yield using 1 and 65% yield using 2 after 6 h). The characterization of the compound matched previous reports: Al-Zoubi, R. M., Marion, O., Hall, D. G. Angew. Chem. Int. Ed. 2008, 47, 2876-2879.

(p (ii) N-benzyl-2-[1-(4-chlorobenzoyl)-5-methoxy-2-methyl-M-indol-3-yl]acetamide

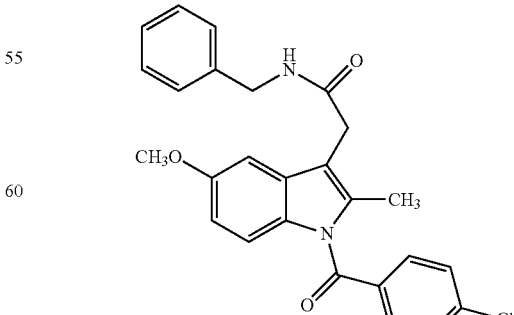

The title compound was prepared using the general procedure for the organocatalytic amidations (62% yield using 1 and 85% yield using 2 after 2 h). The characterization of the compound matched previous reports: Al-Zoubi, R. M., Marion, O., Hall, D. G. Angew. Chem. Int. Ed. 2008, 47, 2876-2879.

(q (i)) (2S)—N-benzyl-2-[4-(2-methylpropyl)phenyl]propanamide

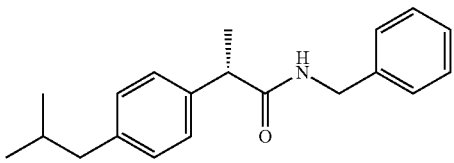 [SMILES: CC(C)Cc1ccc([C@H](C)C(=O)NCc2ccccc2)cc1]

The title compound was prepared using the general procedure for the organocatalytic amidations (70% yield using 1 and 95% yield using 2 after 48 h). The characterization of the compound matched previous reports: Al-Zoubi, R. M., Marion, O., Hall, D. G. Angew. Chem. Int. Ed. 2008, 47, 2876-2879.

(p (ii)) (2S)-2-[4-(2-methylpropyl)phenyl]-N-[(1R)-1-phenylethyl]propanamide

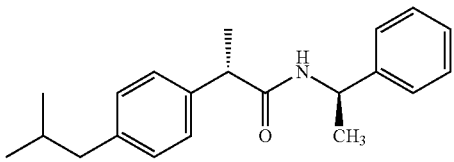 [SMILES: CC(C)Cc1ccc([C@H](C)C(=O)N[C@H](C)c2ccccc2)cc1]

The title compound was prepared using the general procedure for the organocatalytic amidations (52% yield using 1 and 67% yield using 2 after 48 h). The characterization of the compound matched previous reports: Al-Zoubi, R. M., Marion, O., Hall, D. G. Angew. Chem. Int. Ed. 2008, 47, 2876-2879.

Example 20

Amino Acids

The synthesis of various amide bonds using amino acids was investigated using a boronic acid catalyst as presently described. In these reactions, the substrates comprise an N-protected amino acid (the carboxylic acid) and a carboxy-protected amino acid (the amine). These reactions were carried out in accordance with the general reaction conditions described as follows, and the general scheme shown below.

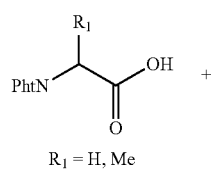

$R_1$ = H, Me

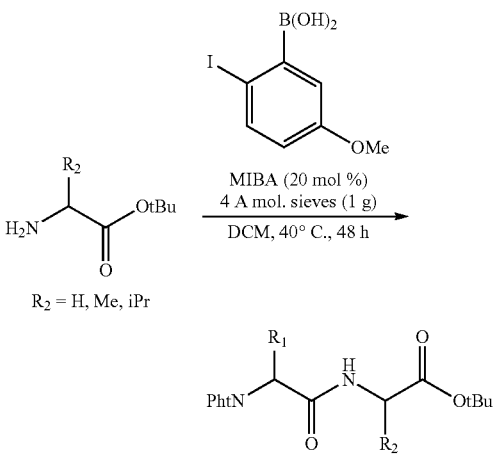

$R_2$ = H, Me, iPr

The carboxylic acid (0.55 mmol, 1.1 equiv), boronic acid (0.1 mmol, 20 mol %) and the amine (0.5 mmol, 1 equiv) were stirred at room temperature (24-25° C.) for 48 h in 7 mL of DCM containing powdered activated 4 Å mol. sieves (1 g). It was found that the results of the reaction was improved by the use of 20 mol % of catalyst instead of 10 mol %. Further improvement was observed by performing the reactions at 40° C. instead of room temperature (approx. 25° C.).

Yields for the reaction of various carboxylic acids and amines are shown in the following table.

| | Amine | | |
|---|---|---|---|
| Acid | H$_2$NGlyOtBu | H$_2$NAlaOtBu | H$_2$NLeuOtBu |
| PhtGlyOH | 79% | 60% | 57% |
| PhtAlaOH | 57% | 43% | 21% |

Example 21

Solvent Screening

Solvent screening was carried out a reactions wherein the substrate comprises an N-protected amino acid (the carboxylic acid) and a carboxy-protected amino acid (the amine) as shown in the following general scheme.

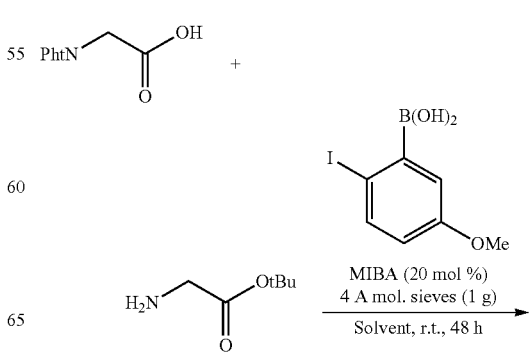

-continued

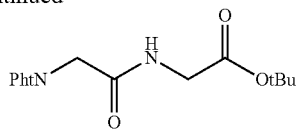

The solvents screened for use with the present method include dichloromethane (DCM), tetrahydrofuran (THF), toluene, nitromethane, methyl-tetrahydrofuran (Me-THF), cyclopentylmethyl ether (CPME), tert-butylmethyl ether (TBME), chlorobenzene and 1,2-dichloroethane (1,2-DME).

The reaction conditions were carried out in accordance with the general procedure as follows. The carboxylic acid (0.55 mmol, 1.1 equiv), boronic acid (0.05 mmol, 10 mol %) and the amine (0.5 mmol, 1 equiv) were stirred at room temperature (24-25° C.) for 48 h in 7 mL of solvent containing powdered activated 4 Å mol. sieves (1 g).

Figure 2:
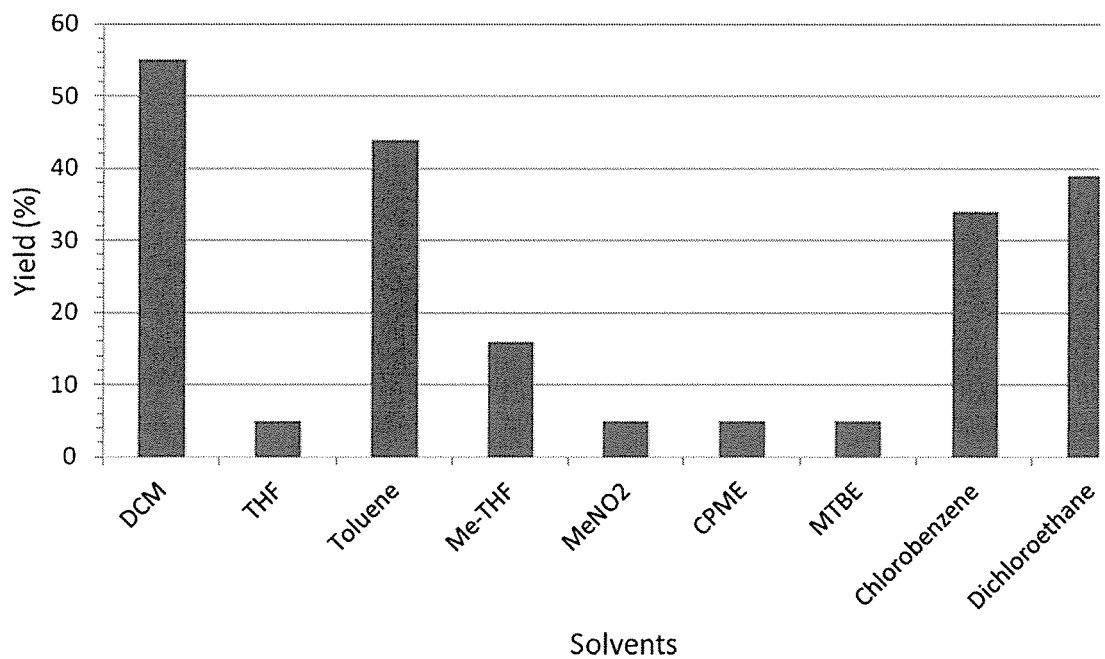
FIG. 2 graphically depicts the results of the solvent screening of Example 21, wherein the percentage yields pertain to the obtained amide for each solvent.

The results are shown in FIG. 2, and in the following table,

| Solvent | DCM | THF | Tol | Me—THF | MeNO$_2$ | CPME | MTBE | Chloro-Benzene | 1,2-DME |
|---|---|---|---|---|---|---|---|---|---|
| Yield (%) | 55 | 5 | 44 | 16 | 5 | 5 | 5 | 34 | 39 |

Example 22

Amidation Using β-Amino-Acids

Boronic acid catalysts as presently described can be used with reactions when one or both of the carboxylic acid and amine are β-amino-acids. An amidation reaction starting with two protected β-amino-acids was investigated using a boronic acid catalyst as presently described. In these reactions, the substrates comprised an N-protected β-amino acid (the carboxylic acid) and a carboxy-protected β-amino acid (the amine). These reactions were carried out in accordance with the general reaction conditions described as follows, and the general scheme shown below.

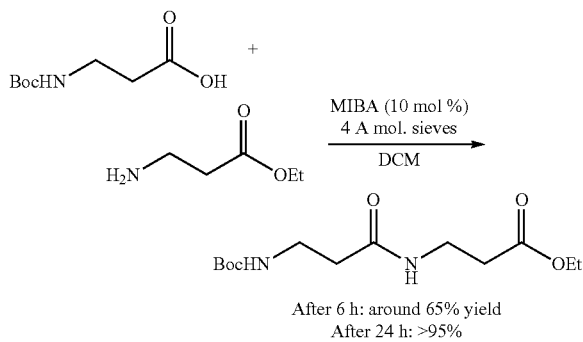

After 6 h: around 65% yield
After 24 h: >95%

The carboxylic acid (0.55 mmol, 1.1 equiv), boronic acid (0.05 mmol, 10 mol %) and the amine (0.5 mmol, 1 equiv) were stirred at room temperature (24-25° C.) in 7 mL of DCM containing powdered activated 4 Å mol. sieves (1 g).

Characterization: $^1$H NMR (300 MHz, CDCl$_3$) δ 6.29 (br, 1H), 5.20 (br, 1H), 4.13 (q, J=7.1 Hz, 2H), 3.49 (dt, J=6.0 Hz, J=6.0 Hz, 2H), 3.56 (dt, J=6.1 Hz, J=6.1 Hz, 2H), 2.50 (t, J=6.2 Hz, 2H), 2.35 (t, J=6.0 Hz, 2H), 1.40 (s, 9H), (t, J=7.1 Hz, 3H). $^{13}$C NMR (100 MHz, CDCl$_3$) δ 172.1, 171.0, 155.6, 78.8, 60.3, 36.2, 35.8, 34.4, 33.6, 28.0, 13.8.

Example 23

Azeotropic Extraction of Water

The present methods can be carried out using the disclosed boronic acid catalysts in combination with various means of removal of water from the reaction. Additionally, in the absence of a means for removing water from the reaction, reasonable yields may still be achieved. An investigation was carried out to compare the yields of the following reaction, shown below, under different conditions involving the removal of water.

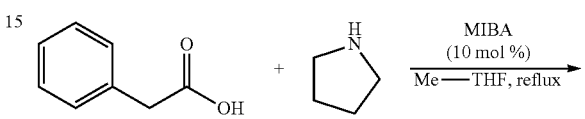

-continued

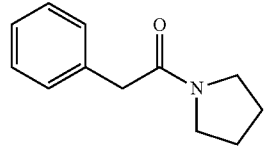

The general reaction conditions were carried out as follows. The carboxylic acid (0.55 mmol, 1.1 equiv), boronic acid (0.05 mmol, 10 mol %) and the amine (0.5 mmol, 1 equiv) were mixed in 7 mL of Me-THF. Runs were carried out using either 4 Å mol. sieves to remove water (runs 1-2), or under reflux using a Dean-Stark apparatus to remove water azeotropically (runs 3-4), or both (runs 5-6). The results of the reactions are shown in the following Table.

| Run | Solvent | Reaction Time (h) | 4 Å Mol. Sieves. | Temperature (° C.) | Yield (%) |
|---|---|---|---|---|---|
| 1 | DCM | 2.5 | Yes (1 g) | 25° C. | 50 |
| 2 | Me—THF | 2.5 | Yes (1 g) | 25° C. | 32 |
| 3 | Me—THF | 8 | No | Reflux | 27 |
| 4 | Me—THF | 24 | No | Reflux | 30 |
| 5 | Me—THF | 4 | Yes (1 g) | Reflux | 65 |
| 6 | Me—THF | 12 | Yes (1 g) | Reflux | 100 |

All publications, patents and patent applications mentioned in this Specification are indicative of the level of skill of those skilled in the art to which this invention pertains and are herein incorporated by reference to the same extent as if each individual publication, patent, or patent application was specifically and individually indicated to be incorporated by reference.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

The embodiments of the invention in which an exclusive property or privilege is claimed are defined as follows:

1. A method for electrophilic activation of a carboxylic acid comprising combining a carboxylic acid-containing compound and a boronic acid compound of formula I, II or III:

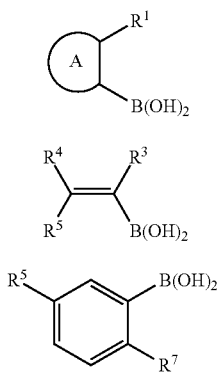

wherein
$R^1$ is a lone pair-containing heteroatom substituent;
A is a 5 or 6-membered heteroaromatic ring comprising at least one heteromoiety selected from O, S, NH or $NC_{1-4}$alkyl in which the $R^1$ and $B(OH)_2$ groups are ortho to each other, and which is optionally substituted with one or more additional substituents independently halo, $R^{2a}$, $OR^{2a}$, $NR^{2a}R^{2b}$, $SR^{2a}$, $S(O)R^{2a}$, $SO_2R^{2a}$, $SeR^{2a}$ or $PR^{2a}R^{2b}R^{2c}$;
$R^{2a}$, $R^{2b}$ and $R^{2c}$ are independently $C_{1-4}$alkyl or $C_{6-10}$aryl;
at least one of $R^3$ and $R^5$ is a lone pair-containing, heteroatom substituent and the other of $R^3$ and $R^5$ is independently H, halo, $R^{6a}$, $C_{1-4}$alkylene$R^{6a}$, $OR^{6a}$, $NR^{6a}R^{6b}$, $SR^{6a}$, $S(O)R^{6a}$, $SO_2R^{6a}$, $SeR^{6a}$ or $PR^{6a}R^{6b}R^{6c}$;
$R^4$ is H, halo, $R^{6a}$, $C_{1-6}$alkylene$R^{6a}$, $OR^{6a}$, $NR^{6a}R^{6b}$, $SR^{6a}$, $S(O)R^{6a}$, $SO_2R^{6a}$, $SeR^{6a}$ or $PR^{6a}R^{6b}R^{6c}$;
$R^{6a}$, $R^{6b}$ and $R^{6c}$ are independently $C_{1-20}$alkyl or $C_{6-14}$aryl;
$R^7$ is halo;
$R^8$ is $OC_{1-6}$alkyl, $OC_{6-10}$aryl or $OC_{1-4}$alkylene$C_{6-10}$aryl; and
each alkyl, aryl and alkylene group is unsubstituted or substituted by one or more halo, $OC_{1-4}$alkyl, $OC_{1-4}$alkylene$C_{6-10}$aryl and/or $OC_{6-10}$aryl,
under conditions for the electrophilic activation of the carboxylic acid.

2. The method of claim 1, wherein:
the boronic acid compound is a compound of formula I; and
A is a 5-membered heteroaromatic ring comprising at least one heteromoiety selected from O, S, NH and $NC_{1-4}$alkyl; or
A is a furan or a thiophene ring; or
A is not substituted with additional substituents.

3. The method of claim 2, wherein $R^1$ is I, Br, Cl or F.

4. The method of claim 2, wherein A is substituted with one or two additional substituents independently selected from halo, $R^{2a}$, $C_{1-4}$alkylene$R^{2a}$, $OR^{2a}$, $SR^{2a}$, $S(O)R^{2a}$ and $SO_2R^{2a}$, wherein $R^{2a}$ is methyl, ethyl or phenyl, and each methyl, ethyl or phenyl is unsubstituted or substituted by one or more halo, $OC_{1-4}$alkyl, $OC_{1-4}$alkylenePh and/or OPh.

5. The method of claim 1, wherein:
the boronic acid compound is a compound of formula II; and
$R^3$ is I, Br, Cl or F; and/or
$R^5$ is I, Br, Cl or F.

6. The method of claim 5, wherein $R^4$ and $R^5$ are independently H, halo, $R^{6a}$, $C_{1-6}$alkylene$R^{6a}$, $OR^{6a}$, $SR^{6a}$, $S(O)R^{6a}$ or $SO_2R^{6a}$, and $R^{6a}$, $R^{6b}$ and $R^{6c}$ are independently $C_{1-10}$alkyl or $C_{6-10}$aryl; and each alkyl, aryl and alkylene group is unsubstituted or substituted by one or more halo, $OC_{1-4}$alkyl, $OC_{1-4}$alkylenePh and/or OPh.

7. The method of claim 6, wherein one of $R^4$ and $R^5$ is an unbranched $C_{1-10}$alkyl and the other is H.

8. The method of claim 1, wherein:
the boronic acid compound is a compound of formula III; and
i) $R^7$ is I; and/or
ii) $R^8$ is OMe, OPh or $OCH_2Ph$ or wherein $R^8$ is $OC_{5-6}$alkyl or $OC_{1-4}$alkylene$C_{6-10}$aryl.

9. The method of claim 1, wherein the method is performed in a solvent comprising at least one of dichloromethane (DCM), tetrahydrofuran (THF) or toluene.

10. The method of claim 1, wherein:
i) the method is carried out at a temperature of between about 20° C. and about 45° C. or between about 50° C. and about 140° C.; and/or
ii) the method is carried out for between about 2 hours and about 50 hours; and/or
iii) the amount of the compound of formula I, II or III is about 1 mol % to about 25 mol %.

11. The method of claim 1, wherein the carboxylic acid is electrophilically activated for reaction with a nucleophile in a nucleophilic 1,2-addition reaction with the carbon atom of the activated carboxylic acid group.

12. A method for electrophilic addition to a carboxylic acid comprising:
(a) obtaining an activated carboxylic acid prepared according to the method of claim 1; and
(b) reacting the activated carboxylic acid with a nucleophile.

13. The method of claim 12, wherein a means for removal of water is:
i) added before or simultaneously with the reaction of the activated carboxylic acid with the nucleophile;
ii) is molecular sieves, wherein the molecular sieves are present during the preparation of the activated carboxylic acid; or
iii) is azeotropic distillation.

14. The method of claim 12, wherein:
i) the ratio of activated carboxylic acid to nucleophile is from about 2:1 to about 1:1; and,
ii) the nucleophile is a compound comprising an amine, an alcohol or a thiol.

15. The method of claim 14, wherein the carboxylic acid and the amine are amino acids, amino acid analogs thereof, or protected versions thereof.

16. The method of claim 14, wherein the compound of formula I, II or II, the activated carboxylic acid, or a nucleophile which is an amine is attached to a solid support.

17. A compound of:
formula III:

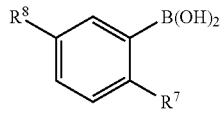

wherein
R$^7$ is I; and
R$^8$ is OC$_{1-6}$alkyl, OC$_{6-10}$aryl or OC$_{1-4}$alkyleneC$_{6-10}$aryl, with the proviso that R$^8$ is not OMe or OBn; or
formula IV:

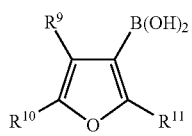

wherein
R$^9$ is I;
R$^{11}$ is H, halo, R$^{12a}$, C$_{1-4}$alkyleneR$^{12a}$, OR$^{12a}$, NR$^{12a}$R$^{12b}$, SR$^{12a}$, S(O)R$^{12a}$, SO$_2$R$^{12a}$, SeR$^{12a}$ or PR$^{12a}$R$^{12b}$R$^{12c}$;
R$^{10}$ is H, halo, R$^{12a}$, C$_{1-4}$alkyleneR$^{12a}$, OR$^{12a}$, NR$^{12a}$R$^{12b}$, SR$^{12a}$, S(O) R$^{12a}$, SO$_2$R$^{12a}$, SeR$^{12a}$ or PR$^{12a}$R$^{12b}$R$^{12c}$;
R$^{12a}$, R$^{12b}$ and R$^{12c}$ are independently C$_{1-4}$alkyl or C$_{6-10}$aryl; and
each alkyl, aryl and alkylene is unsubstituted or substituted by one or more halo, OC$_{1-4}$alkyl, OC$_{1-4}$alkyleneC$_{6-10}$aryl and/or OC$_{6-10}$aryl; or
formula V:

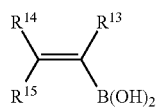

wherein:
R$^{13}$ is I;
R$^{14}$ and R$^{15}$ are independently H, halo, R$^{16a}$, C$_{1-6}$alkyleneR$^{16a}$, OR$^{16a}$, NR$^{16a}$R$^{16b}$, SR$^{16a}$, S(O) R$^{16a}$, SO$_2$R$^{16a}$, SeR$^{16a}$ or SiR$^{16a}$R$^{16b}$R$^{16c}$;
R$^{16a}$, R$^{16b}$ and R$^{16c}$ are independently C$_{1-20}$alkyl or C$_{6-14}$aryl; and
each alkyl, aryl and alkylene group is unsubstituted or substituted by one or more halo, OC$_{1-4}$alkyl, OC$_{1-4}$alkyleneC$_{6-10}$aryl and/or OC$_{6-10}$aryl.

18. A catalyst system comprising a boronic acid compound of formula I, II or III:

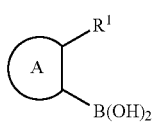

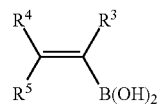

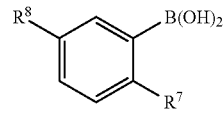

wherein
R$^1$ is a lone pair-containing heteroatom substituent;
A is a 5 or 6-membered heteroaromatic ring comprising at least one heteromoiety selected from O, S, NH or NC$_{1-4}$alkyl in which the R$^1$ and B(OH)$_2$ groups are ortho to each other, and which is optionally substituted with one or more additional substituents independently halo, R$^{2a}$, OR$^{2a}$, NR$^{2a}$R$^{2b}$, SR$^{2a}$, S(O)R$^{2a}$, SO$_2$R$^{2a}$, SeR$^{2a}$ or PR$^{2a}$R$^{2b}$R$^{2c}$;
R$^{2a}$, R$^{2b}$ and R$^{2c}$ are independently C$_{1-4}$alkyl or C$_{6-10}$aryl;
at least one of R$^3$ and R$^5$ is a lone pair-containing, heteroatom substituent and the other of R$^3$ and R$^5$ is independently H, halo, R$^{6a}$, C$_{1-4}$alkyleneR$^{6a}$, OR$^{6a}$, NR$^{6a}$R$^{6b}$, SR$^{6a}$, S(O)R$^{6a}$, SO$_2$R$^{6a}$, SeR$^{6a}$ or PR$^{6a}$R$^{6b}$R$^{6c}$;
R$^4$ is H, halo, R$^{6a}$, C$_{1-6}$alkyleneR$^{6a}$, OR$^{6a}$, NR$^{6a}$R$^{6b}$, SR$^{6a}$, S(O)R$^{6a}$, SO$_2$R$^{6a}$, SeR$^{6a}$ or PR$^{6a}$R$^{6b}$R$^{6c}$;
R$^{6a}$, R$^{6b}$ and R$^{6c}$ are independently C$_{1-20}$alkyl or C$_{6-14}$aryl;
R$^7$ is halo;
R$^8$ is OC$_{1-6}$alkyl, OC$_{6-10}$aryl or OC$_{1-4}$alkyleneC$_{6-10}$aryl; and
each alkyl, aryl and alkylene group is unsubstituted or substituted by one or more halo, OC$_{1-4}$alkyl, OC$_{1-4}$alkyleneC$_{6-10}$aryl and/or OC$_{6-10}$aryl,
wherein:
the boronic acid compound is bound to or adsorbed on a solid support; or
the catalyst system further comprises a means for adsorbing water.

19. A composition comprising:
(a) a boronic acid compound of formula I, II or III:

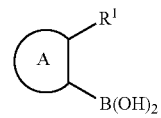

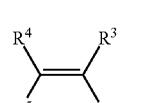

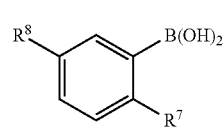

wherein
R$^1$ is a lone pair-containing heteroatom substituent;
A is a 5 or 6-membered heteroaromatic ring comprising at least one heteromoiety selected from O, S, NH or NC$_{1-4}$alkyl in which the R$^1$ and B(OH)$_2$ groups are ortho to each other, and which is optionally substituted with one or more additional substituents independently halo, R$^{2a}$, C$_{1-4}$alkyleneR$^{2a}$, OR$^{2a}$, NR$^{2a}$R$^{2b}$, SR$^{2a}$, S(O)R$^{2a}$, SO$_2$R$^{2a}$, SeR$^{2a}$ or PR$^{2a}$R$^{2b}$R$^{2c}$;
R$^{2a}$, R$^{2b}$ and R$^{2c}$ are independently C$_{1-4}$alkyl or C$_{6-10}$aryl; at least one of R$^3$ and R$^5$ is a lone pair-containing, heteroatom substituent and the other of R$^3$ and R$^5$ is independently H, halo, R$^{6a}$, C$_{1-4}$alkyleneR$^{6a}$, OR$^{6a}$, NR$^{6a}$R$^{6b}$, SR$^{6a}$, S(O)R$^{6a}$, SO$_2$R$^{6a}$, SeR$^{6a}$ or PR$^{6a}$R$^{6b}$R$^{6c}$;
R$^4$ is H, halo, R$^{6a}$, C$_{1-6}$alkyleneR$^{6a}$, OR$^{6a}$, NR$^{6a}$R$^{6b}$, SR$^{6a}$, S(O)R$^{6a}$, SO$_2$R$^{6a}$, SeR$^{6a}$ or PR$^{6a}$R$^{6b}$R$^{6c}$;
R$^{6a}$, R$^{6b}$ and R$^{6c}$ are independently C$_{1-20}$alkyl or C$_{6-14}$aryl; R$^7$ is halo;

R$^8$ is OC$_{5-6}$alkyl or OC$_{1-4}$alkyleneC$_{6-10}$aryl; and
each alkyl, aryl and alylene group is unsubstituted or substituted by one or more halo, OC$_{1-4}$alkyl, OC$_{1-4}$alkyleneC$_{6-10}$aryl and/or OC$_{6-10}$aryl;
(b) a carboxylic acid-containing compound; and
(c) a solvent, wherein the boronic acid compound is present at an amount of about 25 mol% or less, based on the amount of carboxylic acid-containing compound.

20. The composition of claim 19, which additionally comprises a means for adsorbing water.

21. The catalyst system of claim 18, wherein the means for adsorbing water comprises an adsorbent means, molecular sieves, a drying agent, activated alumina, benzophenone, bentonite clay, calcium chloride, calcium hydride, calcium sulfate, copper(II) sulfate, lithium chloride, lithium bromide, magnesium, magnesium sulfate, potassium carbonate, silica gel, sodium chlorate or sodium sulfate, or means for azeotropic distillation.

* * * * *